(12) United States Patent
Tsang et al.

(10) Patent No.: US 9,068,169 B2
(45) Date of Patent: *Jun. 30, 2015

(54) CD56 POSITIVE HUMAN ADULT PANCREATIC ENDOCRINE PROGENITOR CELLS

(75) Inventors: Wen-Ghih Tsang, Sherman Oaks, CA (US); Tianli Zheng, Culver City, CA (US); Wei Liu, Cypress, CA (US)

(73) Assignee: RENEURON, INC., Santa Monica, CA (US)

( * ) Notice: Subject to any disclaimer, the term of this patent is extended or adjusted under 35 U.S.C. 154(b) by 1125 days.

This patent is subject to a terminal disclaimer.

(21) Appl. No.: 12/114,604

(22) Filed: May 2, 2008

(65) Prior Publication Data

US 2009/0246178 A1    Oct. 1, 2009

Related U.S. Application Data

(62) Division of application No. 10/658,437, filed on Sep. 8, 2003, now Pat. No. 7,371,576.

(60) Provisional application No. 60/409,310, filed on Sep. 6, 2002.

(51) Int. Cl.
    *C12N 5/071*     (2010.01)
    *A61K 35/12*     (2015.01)

(52) U.S. Cl.
    CPC .............. *C12N 5/0678* (2013.01); *A61K 35/12* (2013.01); *C12N 2500/34* (2013.01); *C12N 2501/117* (2013.01); *C12N 2501/12* (2013.01); *C12N 2501/599* (2013.01); *C12N 2533/54* (2013.01)

(58) Field of Classification Search
    CPC .................................................. C12N 5/0678
    USPC .......................... 435/378, 370, 373, 375, 384
    See application file for complete search history.

(56) References Cited

U.S. PATENT DOCUMENTS

| | | | |
|---|---|---|---|
| 5,961,972 A | 10/1999 | Dinsmore | |
| 6,326,201 B1 | 12/2001 | Fung et al. | |
| 6,759,039 B2 | 7/2004 | Tsang et al. | |
| 7,371,576 B2 | 5/2008 | Tsang et al. | |

FOREIGN PATENT DOCUMENTS

| | | | |
|---|---|---|---|
| WO | WO-97/15310 A1 | 5/1997 | |
| WO | WO-00/78929 A1 | 12/2000 | |
| WO | WO-02/02750 A1 | 1/2002 | |

OTHER PUBLICATIONS

Ami, K. at al. (2002). "Activation of Human T cells with NK Cell Markers by Staphylococcal Enterotoxin A via Il-12 but not Vial Il-18," *Clinical and Experimental Immunology* 128:453-459.

Barton, C.H. et al. (1988). "Complete Sequence and in vitro Expression of a Tissue-specific Phosphatidylinositol-linked N-CAM Isoform from Skeletal Muscle," *Development* 104(1):165-173.
Cunningham, B. et al. (1987). "Neural Cell Adhesion Molecule: Structure, Immunoglobulin-like Domains, Cell Surface Modulation, and Alternative RNA Splicing," *Science* 236:799-806.
Doyle, M. at al. (2001). "Glucagon-like Peptide-1," *Recent Progress in Hormone Research* 56:377-399.
Gahr, S. at al. (2002). "Hepatocyte Growth Factor Stimulates Proliferation of Pancreatic β-cells Particularly in the Presence of Subphysiological Glucose Concentrations," *Journal of Molecular Endocrinology* 28(2): 99-110.
Garcia-Ocana, A. et al. (2000). "Hepatocyte Growth Factor Overexpression in the Islet of Transgenic Mice Increases Beta Cell Proliferation, Enhances Islet Mass, and Induces Mild Hypoglycemia," *The Journal of Biological Chemistry* 275(2):1226-1232.
Goke, R. at al. (1993). "Exendin-4 Is a High Potency Agonist and Truncated Exendin-(9-30)-amide an Antogonist at the Glucagon-like Peptide 1-(7-36)-amide Receptor of Insulin-secreting β-Cells," *The Journal of Biological Chemistry* 268(26):19650-19655.
Hemperly, J. et al. (1990). "Characterization of cDNA Clones Defining Variant Forms of Human Neural Cell Adhesion Molecule N.-CAM," *Journal of Molecular Neuroscience* 2:71-78.
Hung, G. et al. (2002). "Immunohistochemistry Study of Human Vestibular Nerve Schwannoma Differentiation," *Glia* 38:363-370.
Krakowski, M. et al. (1999). "Pancreatic Expression of Keratinocyte Growth Factor Leads to Differentiation of Islet Hepatocytes and Proliferation of Duct Cells," *American Journal of Pathology* 154(3):683-691.
Krakowski, M. et al. (1999). "Transgenic Expression of Epidermal Growth Factor and Keratinocyte Growth Factor in β-cells Results in Substantial Morphological Changes," *Journal of Endocrinology* 162(2):167-175.
Leon, C. et al. (1992). "Expression of Cell Adhesion Molecules and Catecholamine Synthesizing Enzymes in the Developing Rat Adrenal Gland," *Developmental Brain Research* 70:109-121.
Mashima, H. et al. (1996). "Formation of Insulin-Producing Cells from Parcreatic Acinar AR42J Cells by Hepatocyte Growth Factor," *Endocrinology* 137(9):3969-3976.
Mechtersheimer, G. et al. (1992). "Expression of the Natural Killer (NK) Cell-Associated Antigen CD56(Leu-19), Which is Identical to the 140-kDa Isoform of N-CAM, in Neural and Skeletal Muscle Cells and Tumors Derived Therefrom," *Annals of the New York Academy of Sciences* 650:311-316.
Ou, D. et al. (2002)."β-Cell Antigen-Specific CD56+ NKT Cells From Type 1 Diabetic Patients: Antoaggressive Effector T Cells Damage Human CD56+ β Cells by HLA-Restricted and Non-HLA-Restricted Pathways," *Human Immunology* 63:256-270.
Peck, A. (2001). "Pancreatic Stem cells: Building Blocks for a Better Surrogate Islet to Treat Type 1 Diabetes," *Annals of Medicine* 33(3):186-192.
Pierre, K. et al. (2001). "The Polysialylated Neural Cell Adhesion Molecule Reaches Cell Surfaces of Hypothalamic Neurons and Astrocytes Via The Constitutive Pathway," *Neuroscience* 103(1):133-142.
Rabinowitz, J. et al. (1996). "Targeted Mutation of Ncam to Produce a Secreted Molecule Results in a Dominant Emryonic Lethality," *Proceedings of the National Academy of Science USA* 93:6421-6424.

(Continued)

*Primary Examiner* — Ruth Davis
(74) *Attorney, Agent, or Firm* — Morrison & Foerster LLP

(57) ABSTRACT

The invention relates to the discovery of a selective cell surface marker that permits the selection of a unique subset of pancreatic stems cells having a high propensity to differentiate into insulin producing cells or into insulin producing cell aggregates.

14 Claims, 4 Drawing Sheets

(56) References Cited

OTHER PUBLICATIONS

Saito, S. et al. (1994). "Complementary DNA Sequence Encoding the Major Neural Cell Adhesion Molecule Isoform in a Human Small Cell Lung Cancer Cell Line," *Lung Cancer* 10(5-6):307-318.

Shilakhovenko et al. (1991). "Use of Ultrasound Amplitude Histography in the Diagnosis of Chronic Pancreatitis," *Vrachebnoe Delo* 2:453-459.

Shipley et al. (1997). "Paraffin Immunohistochemical Detection of CD56, a Useful Marker for Neural Cell Adhesion Molecule (NCAM), in Normal and Neoplastic Fixed Tissues," *Applied Immunohistochemistry & Molecular Morphology* 5(2):87-93.

Soria, B. et al. (2001). "From Stem Cells to Beta Cells: New Strategies in Cell Therapy of Diabetes Mellitus," *Diabetologia* 44:407-415.

Yang, L. et al.; "In vitro Trans-differentiation of Adult Hepatic Stem Cells into Pancreatic Endocrine Hormone-producing Cells," *Proceedings of the National Academy of Science USA* 99(12):8078-8083.

MATURATION MEDIA (MM)

| Component | mg/L |
|---|---|
| DMEM/F12 | |
| D-GLUCOSE | 1550 |
| L-GLUTAMINE | 0.5mM |
| | 2440 |

| COMPONENT | μg/mL |
|---|---|
| INSULIN | 500 |
| HUMAN TRANSFERRIN | 10,000 |
| PROGESTERONE | 0.63 |
| PUTRESCINE | 1.611 |
| SELENITE | 0.52 |

| COMPONENT | mg/L |
|---|---|
| AMINO ACIDS | |
| L-ALANINE | 2 |
| L-GLUTAMATE | 3.7 |
| L-GLUTAMINE | 441 |
| L-PROLINE | 7.76 |

| VITAMINS | |
|---|---|
| BIOTIN | 0.1 |
| VIT. B12 | 0.34 |
| HORMONES | |
| CORTICOSTERONE | 0.02 |
| PROGESTERONE | 0.0063 |
| VIT. A | 0.1 |
| RETINOL ACETATE | 0.1 |
| INSULIN | 4 |
| T3 | 0.002 |

| ANTIOXIDANTS | |
|---|---|
| Na PYRUVATE | 25 |
| LIPOID ACID | 0.047 |
| VIT. E | 1 |
| CATALASE | 2.5 |
| GLUTATHIONE | 1 |
| SUPEROXIDE DISMUTASE | 2.5 |

| OTHER | |
|---|---|
| L-CARNITINE | 2 |
| ETHANOLAMINE | 1 |
| D(+)-GALACTOSE | 15 |
| HEPES | 2,600 |
| PUTRESCINE | 16.1 |
| PENICILLIN | 50 IU/mL |
| STREPTOMYCIN | 0.5 |
| SELENIUM | 0.016 |
| ZnSO4 | 0.194 |
| LINOLEIC ACID | 1 |
| LINOLENIC ACID | 1 |
| BOVINE ALBUMINE | 2500 |
| TRANSFERRIN | 5 |

FIG. 3

CD56 POSITIVE HUMAN ADULT PANCREATIC ENDOCRINE PROGENITOR CELLS

CROSS REFERENCE TO RELATED APPLICATIONS

This application is a divisional application of U.S. Ser. No. 10/658,437, filed Sep. 8, 2003, entitled "CD56 POSITIVE HUMAN ADULT PANCREATIC ENDOCRINE PROGENITOR CELLS," which claims the benefit of U.S. Provisional Application No. 60/409,310; filed Sep. 6, 2002, entitled "CD56 POSITIVE HUMAN ADULT PANCREATIC ENDOCRINE PROGENITOR CELLS," both of which are herein incorporated by reference in their entirety for all purposes.

FIELD OF THE INVENTION

The invention relates to the discovery of a selective cell surface marker that permits the selection of a unique subset of pancreatic stems cells having a high propensity to differentiate into insulin producing cells or into insulin producing cell aggregates.

BACKGROUND OF THE INVENTION

In attempting to cultivate adult pancreatic islet cells, the objective has long been to isolate pancreatic progenitor cells that are capable of proliferation and differentiation into pancreatic β cells. One important step in isolation of pancreatic progenitor cells would be to identify recognizable cell markers, specific for the progenitor cells. Both intracellular and extracellular markers have been investigated for this purpose.

Once identified, extracellular markers would offer the advantage that the cells expressing the marker can be sorted under sterile conditions and kept alive to continue their study. Epithelial cell adhesion molecules such as Ep-CAM and integrins have been investigated as pancreatic islet progenitor markers. See e.g., Cirulli et al., J. Cell Biol. 140:1519-1534 (1998); and Cirulli et al., J. Cell Biol. 150:1445-1460 (2000). Cells selected by these makers have been shown to express transcription factors, such as PDX-1, indicating that they belong to the cell lineage in pancreatic development. However those cells have not been shown to be able to produce endocrine hormones such as insulin. Id.

Intracellular markers, particularly those from embryonic cells that develop into mature islet cells, have been extensively studied as progenitor markers. Transcription factors such as PDX-1, Ngn3, and H1xb9, for example, have been studied. They are expressed in cells that are programmed during embryonic development to become pancreatic endocrine cells. However, these intracellular markers offer less practical value than extracellular makers in selecting progenitor cells, because analysis of expression of those markers requires either the killing the cells or permanent modification of the cells by genetic engineering of reporter genes into the cells.

Thus, there is a great need to identify extracellular marker(s) that allow the identification and selection of human adult pancreatic endocrine progenitor cells. The present invention solves this and other problems.

BRIEF SUMMARY OF THE INVENTION

This invention provides cell cultures of propagating pancreatic cells comprising progenitors of insulin producing pancreatic β cells. At least 50% of the cells exhibit the CD56 molecule as a cell surface marker and have an insulin:actin mRNA ratio less than 1:1. In one embodiment, at least 70% of the cells exhibit the CD56 molecule as a cell surface marker and have an insulin:actin mRNA ratio less than 1:1. In a further embodiment, at least 70% of the cells exhibit the CD56 molecule as a cell surface marker and have an insulin:actin mRNA ratio less than 1:100. In another embodiment, at least 90% of the cells exhibit CD56 as a cell surface marker and have an insulin:actin mRNA ratio less than 1:100. The invention also encompasses a cell culture of insulin producing cell aggregates produced from the propagating pancreatic progenitor cell culture.

This invention also includes a method of obtaining the culture of propagating pancreatic cells by isolating from a pancreas, and contacting the cells with a CD56 binding reagent to allow selection of CD56 positive pancreatic cells and separation of CD56 positive cells from CD56 negative cells. In some embodiments, the CD56 binding reagent is labeled. In some embodiments, the step of selecting is done by fluorescence activated cell sorting. In some embodiments, the step of selecting is done by panning. In one embodiment, CD56 binding reagent is an antibody that specifically binds to the CD56 protein. In one embodiment, the CD56 binding reagent is an antibody that specifically binds to an oligosaccharide linked to the CD56 protein. In another embodiment, the CD56 binding reagent is a lectin that specifically binds to an oligosaccharide linked to the CD56 protein. In another embodiment, the CD56 binding reagent is a ligand of the CD56 protein. In a further embodiment, the ligand is selected from the group consisting of soluble CD56, heparin, and heparin sulfate. In one embodiment, the pancreas is from a human.

In a further aspect of the invention, the CD56 positive pancreatic cells are propagated and differentiated into an aggregate of insulin producing cells. In some embodiments, the step of differentiating the cells comprises culturing the cells on plates coated with collagen IV. In one embodiment, the step of differentiating the cells comprises culturing the cells in a media comprising a differentiation factor. Many differentiation factors can be used including hepatocyte growth factor, keratinocyte growth factor, exendin-4, basic fibroblast growth factor, insulin-like growth factor-I, nerve growth factor, epidermal growth factor and platelet-derived growth factor.

The invention also includes a method of producing an aggregate of insulin producing pancreatic cells by isolating from a pancreas, contacting the cells with a CD56 binding reagent to allow selection of CD56 positive propagating pancreatic cells and separation of CD56 positive cells from CD56 negative cells, and differentiating the CD56 positive propagating pancreatic cell culture into an aggregate of insulin producing pancreatic cells. In some embodiments, the CD56 binding reagent is labeled. In some embodiments, the step of selecting is done by fluorescence activated cell sorting. In some embodiments, the step of selecting is done by panning. In one embodiment, CD56 binding reagent is an antibody that specifically binds to the CD56 protein. In one embodiment, the CD56 binding reagent is an antibody that specifically binds to an oligosaccharide linked to the CD56 protein. In another embodiment, the CD56 binding reagent is a lectin that specifically binds to an oligosaccharide linked to the CD56 protein. In another embodiment, the CD56 binding reagent is a ligand of the CD56 protein. In a further embodiment, the ligand is selected from the group consisting of soluble CD56, heparin, and heparin sulfate. In one embodiment, the pancreas is from a human. In some embodiments, the step of differentiating the cells comprises culturing the cells on plates coated with collagen IV. In one embodiment, the step of differentiating the cells comprises culturing the cells in a media comprising a differentiation factor. In another embodiment, the differentiation factor is selected from the group consisting of hepatocyte growth factor, keratinocyte growth factor, exendin-4, basic fibroblast growth factor, insulin-like growth factor-I, nerve growth factor, epidermal growth factor and platelet-derived growth factor.

The invention also encompasses a method of providing pancreatic endocrine function to a mammal in need of such function, by isolating a CD56 positive propagating cell culture, and implanting into a mammal the CD56 positive propagating cell culture in an amount sufficient to produce a measurable amount of insulin in the mammal. In a further embodiment the CD56 positive propagating cell culture differentiates further into insulin producing cells in vivo, e.g., within the mammal. In another embodiment, the CD56 positive propagating cell culture is differentiated into insulin producing aggregates in vitro, and then the aggregates of insulin producing pancreatic cells are implanted into the mammal in an amount sufficient to produce a measurable amount of insulin in the mammal. In one embodiment, the mammal is a human. In another embodiment, a human pancreas is used as a source of the CD56 positive propagating cell culture.

The invention also encompasses a method of monitoring a culture of propagating pancreatic cells by contacting the pancreatic cells with a CD56 binding reagent; and determining the quantity of cells that exhibit CD56 as a cell surface marker. In one embodiment, the detecting step is done by fluorescence activated cell sorting. In another embodiment, the CD56 binding reagent is an antibody that binds specifically to the CD56 protein. Monitoring the propagating pancreatic cell culture is useful to determine the potential of the culture to form aggregates of insulin producing cells.

BRIEF DESCRIPTION OF THE DRAWINGS

FIG. 3 provides the composition of maturation media (MM).

DEFINITIONS

Figure 1:
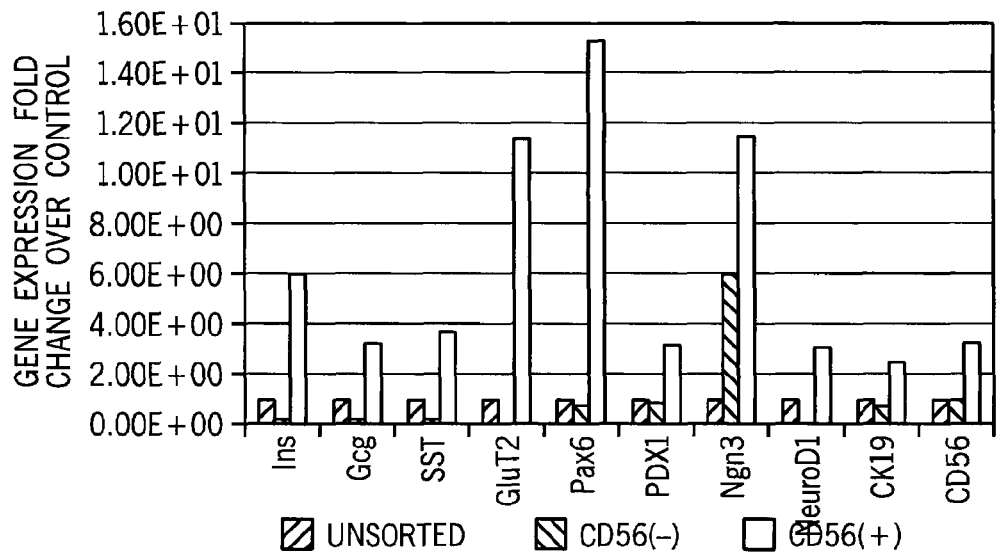
FIG. 1 demonstrates the relative gene expression levels of unsorted cells, CD56 positive cells and CD56 negative cells. Gene expression was expressed as a ratio of mRNA copy number of the gene of interest (such insulin mRNA copy number) over that of β-actin (mRNA copy number of β-actin). For comparison, the levels of gene expression expressed by unsorted cells were normalized to 1, while the levels of gene expressions expressed by CD56 positively sorted and negatively sorted cells were plotted as folds of increase or decrease relative to that of unsorted cells.

As used herein, a "cell culture of propagating pancreatic cells" is a culture of cells derived from pancreatic tissue that is able to undergo cell division and to be passaged from one culture vessel to another over time. A culture of propagating pancreatic cells that exhibits CD56 as a cell surface marker refers to a culture of pancreatic progenitor cells that, in addition to detectable CD56 cell surface expression, exhibits low levels of insulin mRNA and is capable of differentiation into mature pancreatic cells, including insulin-producing pancreatic β cells. In some embodiments the CD56 positive pancreatic cells have insulin:actin mRNA ratios less than 1:1. Other insulin:actin mRNA ratios are also encompassed by the present invention, e.g., 1:50, 1:20, 1:10, 1:5, and 1:2. In some embodiments, the CD56 positive pancreatic cells have insulin:actin mRNA ratios less than 1:100. In some embodiments the insulin mRNA levels in CD 56 positive propagating progenitor cells will only be detectable using very sensitive methods, e.g., in situ hybridization.

As used herein, "CD56 protein" refers to a cell surface glycoprotein thought to play a role in embryogenesis, development, and contact mediated interactions between cells. Because of differential transcript splicing, the majority of CD56 protein are found in three major sizes: 180 kDa, 140 kDa, and 120 kDa. Exemplary CD56 proteins include human CD56 proteins, for example the 120 kDal form, Accession Number P13592; the 140 kDal form, Accession Number P13591, and the 180 kDal form, see e.g., Hemperly, J. et al., J. Mole Neurosci. 2:71-78 (1990).

The term "CD56 binding reagent" is used herein to refer to a compound that specifically binds to a CD56 protein or to molecules covalently linked to a CD56 protein, such as oligosaccharides. In a preferred embodiment, the CD56 binding reagent is an antibody that specifically binds to the CD56 protein. The term "CD56 binding reagent" also encompasses compounds that are specifically bound by the CD56 protein, for example heparin and heparin sulfate. The term encompasses ligands and lectins as defined herein. CD56 binding reagents are used to identify or select cells that express CD56 protein as a cell surface marker.

Cells that "exhibit CD56 as a cell surface marker" are cells that exhibit a sufficient quantity of CD56 on the cell surface to allow the cells to be selected or picked out from a population of cells using conventional CD56 specific binding reagents and methods described herein, such as FACS, immunocytochemistry, immunoadsorbtion, and panning. In a preferred embodiment a CD56 antibody is used to select cells that "exhibit CD56 as a cell surface marker."

"Insulin:actin mRNA ratios are measured by band density using gel scanner or by real time PCR using different labels for insulin and actin. With these methods, insulin:actin mRNA ratios are an average across a population of cells. Insulin:actin mRNA rations can also be measured on an individual cell basis using in situ hybridization.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer* Therapy, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121: 210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332:323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to CD56 proteins, polymorphic variants, alleles, orthologs, and conservatively modified variants, or splice variants, or portions thereof, can be selected to obtain only those polyclonal antibodies that are specifically immunoreactive with CD56 proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Specific binding can also be used to describe the interaction of other molecules that specifically bind to CD56 protein, e.g. CD56 ligands and lectins that recognize CD56.

An "antigen" is a molecule that is recognized and bound by an antibody, e.g., peptides, carbohydrates, organic molecules, or more complex molecules such as glycolipids and glycoproteins. The part of the antigen that is the target of antibody binding is an antigenic determinant and a small functional group that corresponds to a single antigenic determinant is called a hapten.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

As used herein, "insulin producing cells" refers to cells that secrete detectable amounts of insulin. "Insulin producing cells" can be individual cells or collections of cells. One example of a collection of "insulin producing cells" is "insulin producing cell aggregates" e.g., an organized collection of cells with a surrounding mantle of CK-19 positive cells and an inner cell mass. "Aggregate" in the context of cells refers to a three dimensional structure. "CK-19" is a 40 kD acidic keratin, cytokeratin 19. "Mantle" refers to an envelope of cells surrounding in three dimensions the inner cell mass.

The term "contacting" is used herein interchangeably with the following: combined with, added to, mixed with, passed over, incubated with, flowed over, etc.

An "oligosaccharide linked to CD56" is a polysaccharide molecule that is covalently linked to the CD56 protein. In a preferred embodiment, the oligosaccharide is 30 linked through an asparagine residue.

The term "lectin" refers to protein that recognize specific carbohydrate molecules. In a preferred embodiment the carbohydrate is all or part of an oligosaccharide linked to a CD56 protein molecule.

A "ligand" is a molecule that is specifically bound by a protein. As an example, heparin and heparin sulfate are bound by the CD56 molecule. The term also encompasses molecules that bind to a protein, for example, an antibody that specifically binds to a protein. In some instances the ligand binds to a molecule that is covalently linked to a protein, for example, a carbohydrate or an oligosaccharide.

The terms "heparan or heparin and heparin sulfate" are known to those of skill in 10 the art. Heparin and heparin sulfate are examples of glycosaminoglycans.

The term "FACS" refers to fluorescence activated cell sorting, a technique used to separate cells according to their content of particular molecules of interest. The molecule of interest can be specific for a type of cell or for particular cell state. The molecule of interest can be fluorescently labeled directly by binding to a fluorescent dye, or by binding to a second molecule, which has been fluorescently labeled, e.g., an antibody or lectin that has been fluorescently labeled and that specifically binds to the molecule of interest. In a preferred embodiment, a fluorescently labeled CD56 specific antibody is used to separate CD56 positive cells from CD56 negative cells.

The term "panning" refers to a method of selecting cells that bind to a CD56 binding reagent. A flat surface, e.g., a culture dish, is coated with a CD56 binding reagent. Pancreatic cells are added to the surface and allowed to bind to the CD56 binding reagent. The culture dishes are then washed, removing the CD56 negative cells from the dish. In a preferred embodiment, a CD56 specific antibody is used to coat a culture dish and "pan" for CD56 positive cells in a population of pancreatic cells.

"Differentiate" or "differentiation" refers to a process where cells progress from an undifferentiated state to a differentiated state or from an immature state to a mature state. For example, undifferentiated pancreatic cells are able to proliferate and express characteristics markers, like PDX-1. Mature or differentiated pancreatic cells do not proliferate and secrete high levels of pancreatic endocrine hormones. E.g., mature β-cells secrete insulin at high levels. Changes in cell interaction and maturation occur as cells lose markers of undifferentiated cells or gain markers of differentiated cells. Loss or gain of a single marker can indicate that a cell has "matured or differentiated."

The term "differentiation factors" refers to a compound added to pancreatic cells to enhance their differentiation to mature insulin producing β cells. Exemplary differentiation factors include hepatocyte growth factor, keratinocyte growth factor, exendin-4, basic fibroblast growth factor, insulin-like growth factor-I, nerve growth factor, epidermal growth factor and platelet-derived growth factor.

The term "providing pancreatic function to a mammal in need of such function" refers to a method of producing pancreatic hormones within the body of a mammal unable to produce such hormones on its own. In a preferred embodiment, insulin is produced in the body of a diabetic mammal. The pancreatic function is provided by implanting or transplanting aggregates of insulin producing pancreatic cells, produced by the methods of this disclosure into the mammal. The number of aggregates implanted is an amount sufficient to produce a measurable amount of insulin in the mammal. The insulin can be measured by Western blotting or by other detection methods known to those of skill in the art, including assays for insulin function, such as maintenance of blood glucose levels. Insulin can also be measured by detecting C-peptide in the blood. In another preferred embodiment, the provision of pancreatic function is sufficient to decrease or eliminate the dependence of the mammal on insulin produced outside the body.

"Encapsulation" refers to a process where cells are surrounded by a biocompatible acellular material, such as sodium alginate and polylysine. Preferably small molecules, like sugars and low molecular weight proteins, can be taken up from or secreted into an environment surrounding the encapsulated cells. At the same time access to the encapsulated cells by larger molecules and immune cells is limited.

"Implanting" is the grafting or placement of the cells into a recipient. It includes encapsulated cells and non-encapsulated. The cells can be placed subcutaneously, intramuscularly, intraportally or interperitoneally by methods known in the art.

A "population" of cells refers to a plurality of cells obtained by a particular isolation or culture procedure. While the selection processes of the present invention yield populations with relatively uniform properties, a population of cells may be heterogeneous when assayed for marker expression or other phenotype. Properties of a cell population are generally defined by a percentage of individual cells having the particular property (e.g., the percentage of cells staining positive for a particular marker) or the bulk average value of the property when measured over the entire population (e.g., the amount of mRNA in a lysate made from a cell population).

"Passage" of cells usually refers to a transition of a seeded culture container from a partially confluent state to a confluent state, at which point they are removed from the culture container and reseeded in a culture container at a lower density. However, cells may be passaged prior to reaching confluence. Passage typically results in expansion of the cell population as they grow to reach confluence. The expansion of the cell population depends on the initial seeding density but is typically a 1 to 10, 1 to 5, 1 to 3, or 1 to 2 fold expansion.

Thus, passaging generally requires that the cells be capable of a plurality of cell divisions in culture.

DETAILED DESCRIPTION OF THE INVENTION

I. Introduction

For the first time, the CD56 protein, also known as Neural Cell Adhesion Molecule (N-CAM) has been shown to be an extracellular marker for progenitors of pancreatic β cells. CD56 was originally isolated from developing neural tissue, but is also found in normeural tissues. CD56 is expressed on neurons, muscle cells, adrenal medulla cells, astrocytes, Schwann cells, NK cells and a subset of activated T cells including those that are β cell antigen-specific and known to cause Type 1 diabetes. See e.g., Shliakhovenko et al., Vrach Delo 2:453-459 (1991); Mechtersheimer et al., Ann. NY Acad. Sci. 650:311-316 (1992); Leon et al., Brain Res. Dev. Brain Res. 70:109-121 (1992); Pierre et al. Neuroscience 103:133-142 (2001); Hung et al. Glai 38:363-370 (2002); and Ami et al., Clin. Exp Immunol. 128:453-459 (2002). CD56 has a developmental role in pattern formation, by facilitating cell-cell interactions. Known binding partners of CD 56 include other CD56 proteins and heparin or heparin sulfate.

CD 56 is a cell surface molecule that is evolutionarily conserved. CD56 family members have been found in chickens, mice, rats, humans, and frogs. The majority of CD56 proteins are found in three isoforms resulting from differential splicing of mRNA: a 180 kDal form, a 140 kDal form, and a 120 kDal form. CD56 proteins are extensively posttranslationally modified. Post translational modifications include addition of asparagine linked oligosaccharides, sulfation of oligosaccharides, phosphorylation of serine and threonine residues, and fatty acid acylation of the protein.

Experiments described herein revel for the first time that CD56 can be used as an extracellular marker of pancreatic progenitor cells. Experiments and examples provided herein also demonstrate that the CD56 positive pancreatic cells identified are capable of being propagated and can also be differentiated into aggregates of insulin producing pancreatic cells.

II. Isolation of CD56 Positive Pancreatic Cells

Those of skill in the art will recognize that a variety of sources and methods can be used to isolate CD56 positive pancreatic cells.

A. Isolation of Pancreas from a Donor

Pancreatic cells isolated for subsequent culturing are obtained from one or more donated pancreases. The methods described herein are not dependent on the age of the donated pancreas. Accordingly, pancreatic material isolated from donors ranging in age from embryos to adults can be used.

In another embodiment, pancreatic cells are isolated from a cultured source. For example, cells prepared according to the microencapsulation method of U.S. Pat. No. 5,762,959 to Soon-Shiong, et al., entitled "Microencapsulation of cells," can be harvested as a source of donor cells.

1. Isolation of Pancreatic Cells from Pancreas

Once a pancreas is harvested from a donor, it is typically processed to yield individual cells or small groups of cells for culturing using a variety of methods. One such method calls for the harvested pancreatic tissue to be cleaned and prepared for enzymatic digestion. Enzymatic processing is used to digest the connective tissue so that the parenchyma of the harvested tissue is dissociated into smaller units of pancreatic cellular material. The harvested pancreatic tissue is treated with one or more enzymes to separate pancreatic cellular material, substructures, and individual pancreatic cells from the overall structure of the harvested organ. Collagenase, DNAse, Liberase preparations (see U.S. Pat. Nos. 5,830,741 and 5,753,485) and other enzymes are contemplated for use with the methods disclosed herein.

Isolated source material can be further processed to enrich for one or more desired cell populations. However, unfractionated pancreatic tissue, once dissociated for culture, can also be used directly in the culture methods of the invention without further separation, and will yield the intermediate cell population. In one embodiment the isolated pancreatic cellular material is purified by centrifugation through a density gradient (e.g., Nycodenz, Ficoll, or Percoll). For example the gradient method described in U.S. Pat. No. 5,739,033, can be used as a means for enriching the processed pancreatic material in islets. The mixture of cells harvested from the donor source will typically be heterogeneous and thus contain α-cells, β-cells, δ-cells, ductal cells, acinar cells, facultative progenitor cells, and other pancreatic cell types.

A typical purification procedure results in the separation of the isolated cellular material into a number of layers or interfaces. Typically, two interfaces are formed. The upper interface is islet-enriched and typically contains 10 to 100% islet cells in suspension. The second interface is typically a mixed population of cells containing islets, acinar, and ductal cells. The bottom layer is the pellet, which is formed at the bottom of the gradient. This layer typically contains primarily (>80%) acinar cells, some entrapped islets, and some ductal cells. Ductal tree components can be collected separately for further manipulation.

The cellular constituency of the fractions selected for further manipulation will vary depending on which fraction of the gradient is selected and the final results of each isolation. When islet cells are the desired cell type, a suitably enriched population of islet cells within an isolated fraction will contain at least 10% to 100% islet cells. Other pancreatic cell types and concentrations can also be harvested following enrichment. For example, the culture methods described herein can be used with cells isolated from the second interface, from the pellet, or from other fractions, depending on the purification gradient used.

In one embodiment, intermediate pancreatic cell cultures are generated from the islet-enriched (upper) fraction. Additionally, however, the more heterogeneous second interface and the bottom layer fractions that typically contain mixed cell populations of islets, acinar, and ductal cells or ductal tree components, acinar cells, and some entrapped islet cells, respectively, can also be used in culture. While both layers contain cells capable of giving rise to the CD56 positive population described herein, each layer may have particular advantages for use with the disclosed methods.

B. Selection of CD56 Positive Pancreatic Cells

Once a source of pancreatic cells have been chosen, CD56 positive cells can be selected and then separated from cells that do not express CD56. Those of skill in the art will recognize that a variety of methods can be used to select CD56 positive cells and separate those cells from CD56 negative cells.

1. Detection of CD56 Positive Cells Using Molecules that Bind CD56

Those of skill in the art will recognize that there are many methods to detect CD56 protein. For example, antibodies that bind specifically to the CD56 protein can be used to detect CD56. Antibodies specific to the CD56 protein are known to those of skill in the art and are commercially available from, for example, Research Diagnostics, Inc.; Abam; Ancell Immunology Research Products; eBioscience; the Hybridoma Bank of the University of Iowa; and Zymed Laboratories, Inc. Antibodies that recognize the extracellular portion of CD56 can be used in the present invention.

The CD 56 protein is extensively post-translationally modified. Antibodies can also be used to detect molecules added as part of those modifications, e.g., sugars and oligosaccharide molecules.

In addition to antibodies, other molecules that bind specifically to CD56 can be used to identify CD56 positive cells. For example, lectins are molecules that bind specifically to particular sugars or oligosaccharides. Lectins that bind specifically to CD56 can be used in the present invention. CD56 also binds specifically to particular ligands, including other CD56 proteins and heparin or heparin sulfate. These, too, can be used to practice the present invention.

Those of skill in the art will recognize that molecules that bind specifically to CD56 are particularly useful if they are labeled and thus able to be detected by some means. A "label" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

2. FACS to Select CD56 Positive Cells

Fluorescently labeled molecules that bind specifically to CD56, most commonly antibodies, are used to select CD56 positive cells in conjunction with a Fluorescence Activated Cell Sorter (FACS). Briefly, pancreatic cells are incubated with fluorescently-labeled antibody and after the antibody binding, the cells are analyzed by FACS. The cell sorter passes single cells suspended in liquid through a fluorimeter. The amount of fluorescence is measured and cells with fluorescence levels detectably higher than control, unlabeled, cells are selected as positive cells.

FACS can also be used to physically separate cell populations based on measurement of fluorescence. The flowing cells are deflected by electromagnetic fields whose strength and direction are varied according to the measured intensity of the fluorescence signal. Labeled CD56 positive cells can be deflected into a separate container and thus, separated from unlabeled CD56 negative cells.

After pancreatic cells are isolated from pancreas, the cells are first cultured for one to two passages and then labeled with a CD56 specific antibody. The cells are then scanned using FACS to separate CD56 positive from CD56 negative cells. Up to 80% of the cells are deemed negative for CD56.

While this example has discussed FACS analysis with labeled antibodies, other molecules that specifically bind to CD56, e.g., lectins and other CD56 binding partners, such as other CD56 molecules and heparin or heparin sulfate, can also be used to practice the invention.

Many different fluorescent molecules are available for conjugation to antibodies, for example fluorescein or rhodamine. Those of skill are aware that in some instances more than one extracellular marker can be detected by using different antibodies conjugated to fluorescent molecules. FACS analysis can be done under conditions to identify more than one extracellular marker of interest.

3. Affinity Adsorbing CD56 Positive Cells onto a Solid Support.

CD56 positive cells can also be separated from CD56 negative cells by using CD56 specific binding molecules attached to a solid support. Those of skill in the art will recognize that CD56 specific antibodies can be bound to a solid support through an antibody binding molecule, such as protein G or protein A or alternatively, can be conjugated to a solid support directly. Solid supports with attached CD56 antibodies are commercially available, e.g., StemSep™ and EasySep™, magnetic beads from both from Stem Cell Technologies.

CD56 positive cells can also be separated from CD56 negative cells through the technique of panning. Panning is done by coating a solid surface with a CD56 binding reagent and incubating pancreatic cells on the surface for a suitable time under suitable conditions. A flat surface, e.g., a culture dish, is coated with a CD56 binding reagent. Pancreatic cells are added to the surface and allowed to bind to the CD56 binding reagent. The culture dishes are then washed, removing the CD56 negative cells from the dish. In a preferred embodiment, a CD56 specific antibody is used to coat a culture dish and "pan" for CD56 positive cells in a population of pancreatic cells.

III. Cell Culture and Cultivation of CD56 Positive Cells and their Progeny

A. General Cell Culture Procedures

Once the pancreatic cells are obtained and isolated, they are cultured under conditions that select for propagation of the desired CD56 positive population, or in other embodiments, for the differentiation of more mature cell types. General cell culture methodology may be found in Freshney, *Culture of Animal Cells: A Manual of Basic Technique* 4th ed., John Wiley & Sons (2000). Typically, pancreatic cells are cultured under conditions appropriate to other mammalian cells, e.g., in humidified incubators at 37° C. in an atmosphere of 5% $CO_2$. Cells may be cultured on a variety of substrates known in the art, e.g., borosilicate glass tubes, bottles, dishes, cloning rings with negative surface charge, plastic tissue culture tubes, dishes, flasks, multi-well plates, containers with increased growth surface area (GSA) or Esophageal Doppler Monitor (EDM) finish, flasks with multiple internal sheets to increase GSA, Fenwal bags, and other culture containers.

Once the pancreatic cellular material has been harvested and selected for culture, or once a population is confluent and is to be transferred to a new substrate, a population of cells is seeded to a suitable tissue culture container for cultivation. Seeding densities can have an effect on the viability of the pancreatic cells cultured using the disclosed methods, and optimal seeding densities for a particular culture condition may be determined empirically by seeding the cells at a range of different densities and monitoring the resulting cell survival and proliferation rate. A range of seeding densities has been shown to be effective in producing hormone secreting cells in culture. Typically, cell concentrations range from about $10^2$ to $10^8$ cells per 100 mm culture dish, e.g., $10^2$, $10^3$, $10^4$, $10^5$, $10^6$, $10^7$, or $10^8$ cells per 100 mm culture dish, although lower cell concentrations may be employed for cloning procedures. Cell concentration for other culture vessels may be adjusted by computing the relative substrate surface area and/or medium gas exchange surface area for a different culture vessel. For example, a typical 100 mm culture dish has a substrate surface area of 55 square centimeters (see Freshney, supra), and a cell concentration of 10,000 cells per dish corresponds to about 180 cells per square centimeter, while a cell concentration of 100,000 cells per dish corresponds to about 1,800 cells per square centimeter. Cell concentration in terms of culture vessel surface area may be related to cell concentration in terms of media volume by using the appropriate media volume per culture surface area (0.2-0.5 ml/$cm^2$ are typical ranges for static culture). To determine if a 10 fold expansion has occurred, the cells are removed by enzymatic digestion and counted under microscope in a known volume of fluid. Cells may also be grown on culture surfaces pre-coated with defined extracellular matrix components to encourage growth and differentiation (e.g., fibronectin, Collagen I, Engelbreth-Holm-Swarm matrix, and, preferably, collagen IV or laminin).

Standard cell culture propagation techniques are suitable for practice of the invention. When cells are growing attached to a culture surface, they are typically grown as a monolayer until 80%-90% confluence is reached, at which point the cells are released from the surface by proteolytic digestion and split 1:2 or 1:3 for culture in new vessels. Higher dilutions of the cells are also suitable, generally between the ranges of 1:4 to 1:10, although even lower cell concentrations are appropriate in cloning procedures. Concentrations of proteolytic enzymes and chelating agents are usually lowered when cells are passaged in serum-free media (e.g., 0.025% trypsin and 0.53 mM EDTA). Culture medium is typically changed twice weekly or when the pH of the medium indicates that fresh medium is needed.

The pancreatic cells of the present invention may be cultured in a variety of media. As described herein, media containing or lacking particular components, especially serum, are preferred for certain steps of the isolation and propagation procedures. For example, cells freshly isolated from the pancreas may be maintained in high serum medium to allow the cells to recover from the isolation procedure. Conversely, low serum medium favors the selection and propagation of an intermediate stage population. Accordingly, a number of media formulations are useful in the practice of the invention. The media formulations disclosed here are for exemplary purposes, and non-critical components of the media may be omitted, substituted, varied, or added to simply by assaying the effect of the variation on the replication or differentiation of the cell population, using the assays described herein. See, e.g., Stephan et al., *Endocrinology* 140:5841-54 (1999)).

Culture media usually comprise a basal medium, which includes inorganic salts, buffers, amino acids, vitamins, an energy source, and, in some cases, additional nutrients in the form of organic intermediates and precursors that are involved in protein, nucleic acid, carbohydrate, or lipid metabolism. Basal media include F12, Eagle's MEM, Dulbecco's modified MEM (DMEM), RPMI 1640, a 1:1 mixture of F12 and DMEM, and others. See Freshney, supra. To support the growth of cells, basal medium is usually supplemented with a source of growth factors, other proteins, hormones, and trace elements. These supplements encourage growth, maintenance, and/or differentiation of cells, compensate for impurities or toxins in other medium components, and provide micronutrients lacking in the basal medium. In many culture media, serum is the source of these supplements. Serum can be supplied from a variety of mammalian sources, such as human, bovine, ovine, equine, and the like, and from adult, juvenile, or fetal sources. See Freshney, supra. Fetal bovine serum is a commonly used supplement. Concentrations of serum are expressed in terms of volume of serum as a percentage of the total medium volume, and typically range from about 0.1 to 25%, e.g., about 0.1, 0.2, 0.5, 1, 2, 3, 4, 5, 6, 7, 8, 9, 10, 15, 20, or 25%. In some applications, the basal medium is supplemented with defined or semi-defined mixtures of growth factors, hormones, and micronutrients, rather than with serum. Formulas for serum replacement supplements are disclosed herein; others are known in the art or available from commercial sources (see Freshney, supra). For some embodiments, the concentration of serum is lowered but not eliminated, and defined or semi-defined supplement mixtures are added to the basal medium. Preferred applications for media containing high or low concentrations of serum are described herein.

B. Maintenance and Propagation of Isolated Pancreatic Cells in Media Containing High Serum Cells harvested from a donor pancreas have usually undergone a period of warm or cold ischemia between the death of the donor and the beginning of the isolation procedure. Moreover, during the isolation procedure, pancreatic cells are usually subjected to proteolytic digestion as well as mechanical and shear stresses. Without wishing to be bound by a particular theory, the various traumas experienced by these cells may up-regulate various cellular processes that result in the expansion of pancreatic stem cell populations, such as facultative progenitor cells. Intermediate cell populations may be generated with satisfactory efficiency by placing cells into low serum media directly after isolation or purification. Nonetheless, because the trauma experienced by cells during the isolation procedures may have adverse effects on cell survival and adaptation to culture, it is sometimes desirable to maintain the freshly isolated cells in a stabilizing medium containing high concentrations of serum (e.g., >4%) to improve the efficiency of the culturing process. This maintenance period may be brief (e.g., overnight). Optionally, cells may be maintained for an extended propagation period in high serum medium.

High serum media for stabilization will typically contain at least 4% serum, and, in some embodiments, will contain a higher concentration of serum such as 10% or 20%. Media used for stabilization or propagation may be derived from a basal medium such as RPMI 1640, available from many commercial sources and described by Moore et al., *J Am Med Assoc* 199:519-524 (1967)). Exemplary high serum media for maintenance or propagation include Medium 3 (RPMI 1640+ 10 mM HEPES, 2 mM glutamine, 5 µM $ZnSO_4$, and 10% fetal bovine serum (FBS)) and Medium 7 (RPMI 1640+10 mM HEPES, 2 mM glutamine, 5 µM ZnSO4, and 20% FBS). High serum media may also be derived by mixing a particular volume of high serum medium such as Medium 3 or Medium 7 with a particular volume of serum-free medium such as SM95, SM96, or SM98 (described herein) to arrive at a desired serum concentration (e.g., 4%-9%).

For stabilization after harvest, cells are conveniently cultured in a culture vessel at relatively high densities in a high serum medium (e.g., $10^9$ cells in 70 ml of Medium 7 (20% FBS)). However, lower cell densities and serum concentrations may be employed as well. Cells are typically maintained in the original vessel for a relatively short time (e.g., overnight) to allow for recovery from the harvesting procedure.

Following the maintenance period, cells may be transferred to low serum media for selection and propagation of the CD56 positive cell population as described herein. Optionally, the cells may be cultured in a high serum medium to allow for proliferation of the mixed cell population. In a typical embodiment, cells from the maintenance culture are reseeded into a new culture vessel containing Medium 3 (10% FBS), Medium 7 (20% FBS), or a mixture of Medium 3 and Medium 7 (15% FBS), or other AmCyte culture media. Cells are typically cultured in this medium for 7-10 days, during which time they may grow to confluence. Once the cells have reached confluence, they may be passaged into low serum media for selective expansion of the intermediate cell population described herein.

C. Expansion and Propagation of a CD56 Positive Pancreatic Cell Population by Culture in Media Containing Low Serum Once the pancreatic cells have been isolated, the cells are then transferred to a selective medium to promote the emergence of a propagating intermediate stage population. This selective medium favors propagation of cells which retain the ability to secrete pancreatic endocrine hormones, or which retain the potential to mature into more differentiated cells which secrete high levels of pancreatic endocrine hormones. In general, selective medium will favor propagation of epithelial or epithelial-like cells at the expense of fibroblasts and mesenchymal cells, although pure epithelial cultures have not been shown to be required for the advantageous use of pancreatic cells in the methods of the invention. Typically, epithelial-selective media will yield a population of nearly pure (e.g., <10% fibroblasts or mesenchymal cells) cells after a certain period of growth in culture, e.g., 2, 3, 4, or 5 passages depending on the expansion of the population in each passage.

One type of selective medium which has been employed to favor epithelial cell growth from embryonic tissues is serum-free medium (see, e.g., Stephan et al., supra; Peehl and Ham, *In Vitro* 16:526-40 (1980)). Epithelial-specific media, and, more preferably, low serum media containing a source of growth hormone, may be employed to select for a distinct population of propagating pancreatic cells from adult mammals that retain markers of pancreatic cell development (e.g., PDX-1), but can be further differentiated under appropriate conditions to express high levels of pancreatic endocrine hormones. Particular epithelial-selective media suitable for culture of pancreatic cells are disclosed herein, but other medium formulations known in the art to favor the preferential expansion of epithelial or epithelial-like cells may also be employed.

The transfer to epithelial-selective low serum medium may be accomplished after a period of maintenance in high serum medium ("weaning"), or by transferring the cells directly into selective low serum medium following the isolation and separation procedure ("shock"). Either methodology is suitable for generation of the desired intermediate cell population.

1. Growth Hormones and Preferred Examples

Epithelial selective culture media containing growth hormone (GH) is used promote the emergence of a valuable pancreatic cell population of intermediate differentiation. Without wishing to be bound by a particular theory, it is hypothesized that GH can replace the mitogenic substances ordinarily found in serum that support cell growth, but that serum contains other mitogenic factors that promote the overgrowth of less desirable cell populations (e.g., fibroblasts and mesenchymal cells). Hence, replacement of serum with a supplemental mixture containing GH selects for propagation of a cell population with an intermediate state of differentiation. While the functions of GH in serum-free medium may be substituted with other supplemental ingredients in alternative embodiments of the invention, the ready availability of GH in natural extracts or as recombinant protein makes GH-containing media suitable epithelial-selective media for the methods disclosed herein.

Growth hormones, also known as somatotropins, are polypeptide hormones synthesized in the anterior pituitary which promote normal body growth and lactation and influence various aspects of cellular metabolism. GH has both direct effects on cells and indirect effects mediated by IGF-I and similar molecules; in the intact pancreas, islet cell growth has been connected to the expression of GH and the homologous hormones prolactin and lactogen (see, e.g., Nielsen et al., *J Mol Med* 77(1):62-6 (1999). In humans, mature GH contains 191 amino acid residues and displays a molecular mass of 22 kDa. However, in addition to the commonly observed disulfide dimer, two peptides made of portions of human GH (residues 1-43 and 44-191) have been detected in serum and have distinct effects on adult islet tissue (see Lewis et al., *Endocr J* 47 Suppl:S-8 (2000)). Various naturally occurring derivatives, variants, metabolic products, and engineered derivatives of human GH are known, including glycosylated GH, methionyl GH, 20 kDa GH, acetylated GH, proteolytically cleaved GH, desamido GH, sulfoxide GH, and truncated forms of GH.

GH is a member of a conserved family of hormones including, in humans, GH-V1 and GH-V2, choriomammotropin and prolactin and proteins from other vertebrates such as rodent placental lactogens I and II and other bovine and sheep lactogens, murine proliferin I, II, and III and proliferin-related protein, bovine prolactin-related proteins I, II, and III, rat prolactin-like proteins A and B, and somatolactins from various fishes. Members of this family are characterized by the consensus sequences C-x-[ST]-x(2)-[LIVMFY]-x-[LIVMSTA]-P-x(5)-[TALIV]-x(7)-[LIVMFY]-x(6)-[LIVMFY]-x(2)-[STA]-W or C-[LIVMFY]-x(2)-D-[LIVMFYSTA]-x(5)-[LIVMFY]-x(2)-[LIVMFYT]-x(2)-C.

Growth hormone suitable for practice of the invention may be obtained from a variety of natural and artificial sources. In contrast to therapeutic uses of GH, which often require GH of the same species, GH from a range of primate, mammalian, or vertebrate species may be employed in formulation of low serum media for culture of pancreatic cells. A convenient source of growth hormone is bovine pituitary extract (BPE), which is a rich source of natural GH. BPE (75 μg/ml protein) may be included in the culture medium at about 0.1 to 100 μl/ml, preferably at 0.5 to 50 μl/ml, and most preferably at 5 μl/ml or 37.5 mg/l. Pituitary extracts available from other species (e.g., porcine, ovine, and the like) may also be employed at similar concentrations. Other factors present in pituitary extract may potentiate its effect, but satisfactory results may also be achieved with purified GH, and with recombinant GH. Recombinant bovine and human GH are widely available and are a suitable source of GH activity. Recombinant GH may be added to culture medium at between 0.01 and 100 mg/l, preferably between 0.1 and 10 mg/l, more preferably at about 0.2, 0.5, 0.75, 1, 1.25, 2, or 5 mg/l, and most preferably at about 1.25 mg/L, where 1 mg of recombinant protein is about equivalent to 3 IU of GH.

2. Other Supplements

Typical ingredients added to basal media for complete serum-free media include recombinant human insulin (0.1 to 100 μg/ml), transferrin (0.1 to 100 μg/ml), epidermal growth factor (0.1 to 100 ng/ml), ethanolamine (0.1 to 100 μg/ml), aprotinin (0.1 to 100 μg/ml), glucose (0.1 to 100 mg/ml), phosphoethanolamine (0.1 to 100 μM), triiodothyronone (0.1 to 100 pM), selenium (0.1 to 100 nM), hydrocortisone (0.01 to 100 μM), progesterone (0.1 to 10 nM), forskolin (0.1 to 100 μM), heregulin (0.1 to 100 nM), and bovine pituitary extract (0.1 to 500 μg/ml). Not all supplemental ingredients are required to support cell growth; the optimal concentration or necessity for a particular supplement may be determined empirically, by leaving out or reducing the concentration of a single ingredient and observing the effect on cell proliferation. See e.g., Stephan et al., supra.

In general, supplemental ingredients may be replaced by natural or synthetic products that have the same biological properties. For example, triiodothyronone, hydrocortisone, and progesterone may all be replaced by natural or synthetic hormones known to activate the same intracellular receptors (thyroid receptors, glucocorticoid receptors, and progesterone receptors). Insulin and EGF are typically human proteins produced by recombinant DNA methodology, but may be replaced by polypeptides purified from natural sources, by polypeptides from other species, or by other agonists of the insulin and EGF receptors. GH may, in some cases, be substituted with other antagonists of the GH receptor. Likewise, heregulin, a ligand of the ErbB3 receptor, may be replaced by heregulin isoforms and other ErbB3 agonists such as NRG2, NRG3, and NRG4, sensory and motor neuron-derived factor, neurestin, and Ebp-1, heregulin α, heregulin β, heregulin γ, neuregulin-1 and neuregulin-2 (NRG-1 alpha, NRG-1 beta, NRG-2 alpha, and NRG-2 beta.

Exemplary serum-free media include the basal medium SM96 and the complete medium SM95, which consists of SM96 supplemented as shown in the following tables. SM98 consists of 1:1 F12/DMEM supplemented with a modification of medium supplement 14F described by Stephan et al., supra. SM98 contains less heregulin (1 ng/ml v. 8 ng/ml) than 14F. Thus, SM 98 consists of 1:1 F12/DMEM supplemented with recombinant human insulin, 10 μg/ml; transferrin, 10 μg/ml; epidermal growth factor, 10 ng/ml; ethanolamine, 61 ng/ml; aprotinin, 25 μg/ml; glucose, 5 mg/ml; phosphoethanolamine, 141 ng/ml; triiodothyronone, 3.365 pg/ml; selenium, 4.325 ng/ml; hydrocortisone, 181 ng/ml; progesterone, 3.15 ng/ml; forskolin, 410 ng/ml; heregulin, 1 ng/ml; and bovine pituitary extract, 75 μg/ml. Exemplary sources of EGH and heregulin in SM95 and SM98 are recombinant human EGF (Sigma E9644) and the EGF domain (amino acids 176-246) of human heregulin-β1 (R&D systems 396-HB/CF).

| RPMI 1640 Media (Moore, et al., A.M.A., 199: 519 (1967)) | Mg/L |
|---|---|
| INORGANIC SALTS | |
| $Ca(NO_3)_2$—$4H_2O$ | 100 |
| KCl | 400.00 |
| $MgSO_4$ (anhyd.) | 48.84 |
| NaCl | 5850.00 |
| $Na_2HPO_4$ (anhyd.) | 800.00 |
| OTHER COMPONENTS | |
| D-Glucose | 2000.00 |
| Glutathione (reduced) | 1.0 |
| HEPES | 5958.00 |
| Phenol Red | 5.00 |
| AMINO ACIDS | |
| L-Arginine | 200.00 |
| L-Asparagine (free base) | 50.00 |
| L-Aspartic Acid | 20.00 |
| L-Cystine•2HCl | 65.00 |
| L-Glutamic Acid | 20.00 |
| L-Glutamine | 300.00 |
| Glycine | 10.00 |
| L-Histidine (free base) | 15.00 |
| L-Isoleucine | 50.00 |
| L-Leucine | 50.00 |
| L-Lysine•HCl | 40.00 |
| L-Methionine | 15.00 |
| L-Phenylalanine | 15.00 |
| L-Proline | 20.00 |
| L-Serine | 30.00 |
| L-Threonine | 20.00 |
| L-Tryptophan | 5.00 |
| L-Tyrosine•$2Na_2H_2O$ | 29.00 |
| L-Valine | 20.00 |
| VITAMINS | |
| Biotin | 0.20 |
| D-Ca Pantothenate | 0.25 |
| Choline Chloride | 3.00 |
| Folic Acid | 1.00 |
| i-Inositol | 35.00 |
| Niacinamide | 1.00 |

-continued

| RPMI 1640 Media (Moore, et al., A.M.A., 199: 519 (1967)) | Mg/L |
|---|---|
| Pyridoxine•HCl | 1.00 |
| Riboflavin | 0.20 |
| Thiamine•HCl | 1.00 |
| Thymidine | 0.005 |
| Vitamin $B_{12}$ | 1.04 |

| SM95 | |
|---|---|
| INORGANIC SALTS | |
| $CaCl_2$ | 78.3 |
| $CuSO_4$•$5H_2O$ | 0.00165 |
| $Fe(NO_3)_3$•$9H_2O$ | 0.025 |
| $FeSO_4$•$7H_2O$ | 0.61 |
| KCB | 271 |
| $MgCl_2$ | 28.36 |
| $MgSO_4$ | 39.06 |
| $KH_2PO_4$ | 34 |
| NaCl | 7262.75 |
| $NaHCO_3$ | 1600 |
| $Na_2HPO_4$ | 101.5 |
| $NaH_2PO_4$•$H_2O$ | 31.25 |
| $ZnSO_4$•$7H_2O$ | 0.416 |
| AMINO ACIDS | |
| L-Alanine | 11.225 |
| L-Arginine•HCl | 283.75 |
| L-Asparagine•$H_2O$ | 18.75 |
| L-Aspartic Acid | 16.325 |
| L-Cysteine•$H_2O$(non-animal) | 43.78 |
| L-Cystine•2HCl | 15.65 |
| L-Glutamic Acid | 18.675 |
| L-Glutamax I | 328.5 |
| Glycine | 89.375 |
| Glycyl-Histidyl-Lysine | 0.000005 |
| L-Histidine HCl•$H_2O$ | 38.69 |
| L-Isoleucine | 31.24 |
| L-Leucine | 42.5 |
| L-Lysine•HCl | 82.125 |
| L-Methionine | 13.12 |
| L-Phenylalanine | 22.74 |
| L-Proline | 43.625 |
| L-Serine | 23.625 |
| L-Threonine | 38.726 |
| L-Tryptophan | 6.51 |
| L-Tyrosine•$2Na_2H_2O$ (non-animal) | 35.9 |
| L-Valine | 38.125 |
| OTHER COMPONENTS | |
| D-Glucose | 3000 |
| HEPES | 1787.25 |
| Na Hypoxanthine | 3.2 |
| Linoleic Acid | 0.066 |
| Lipoic Acid | 0.1525 |
| Phenol Red | 4.675 |
| Na Putrescine•2HCl | 0.191 |
| Na Pyruvate | 137.5 |
| VITAMINS | |
| Biotin | 0.037 |
| Ascorbic Acid | 22.5 |
| D-Ca Pantothenate | 1.37 |
| Choline Chloride | 11.49 |
| Folic Acid | 1.826 |
| L-Inositol | 24.3 |
| Niacinamide | 1.03 |
| Pyridoxine•HCl | 1.046 |
| Riboflavin | 0.13 |
| Thiamine•HCl | 1.23 |
| Thymidine | 0.5325 |
| Vitamin $B_{12}$ | 1.04 |
| SUPPLEMENTS | |
| Na Selenous Acid | 0.0034 |
| Epithelial Growth Factor | 0.005 |

-continued

| RPMI 1640 Media (Moore, et al., A.M.A., 199: 519 (1967)) | |
|---|---|
| | Mg/L |
| Ethanolamine | 0.03 |
| Phosphoethanolamine | 0.07 |
| Aprotinin | 12.5 |
| Progesterone | 0.0016 |
| Forskolin | 0.205 |
| HeregulinB | 0.004 |
| Bovine Pituitary Extract | 37.5 |
| Hydrocortisone | 0.0923 |
| r.h. insulin | 5.05 |
| $T_3$ | 0.0000015 |
| L-Thyroxine Na | 0.00002 |
| Bovine Transferrin APG | 7.5 |

SM96

| INORGANIC SALTS | |
|---|---|
| $CaCl_2$ | 78.3 |
| $CuSO_4 \cdot 5H_2O$ | 0.00165 |
| $Fe(NO_3)_3 \cdot 9H_2O$ | 0.025 |
| $FeSO_4 \cdot 7H_2O$ | 0.61 |
| KCl | 271 |
| $MgCl_2$ | 28.36 |
| $MgSO_4$ | 39.06 |
| $KH_2PO_4$ | 34 |
| NaCl | 7262.75 |
| $NaHCO_3$ | 1600 |
| $Na_2HPO_4$ | 101.5 |
| $NaH_2PO_4 \cdot H_2O$ | 31.25 |
| $ZnSO_4 \cdot 7H_2O$ | 0.416 |
| AMINO ACIDS | |
| L-Alanine | 11.225 |
| L-Arginine•HCl | 283.75 |
| L-Asparagine•$H_2O$ | 18.75 |
| L-Aspartic Acid | 16.325 |
| L-Cysteine•$H_2O$(non-animal) | 43.78 |
| L-Cystine•2HCl | 15.65 |
| L-Glutamic Acid | 18.675 |
| L-Glutamax I | 328.5 |
| Glycine | 89.375 |
| Glycyl-Histidyl-Lysine | 0.000005 |
| L-Histidine HCl•$H_2O$ | 38.69 |
| L-Isoleucine | 31.24 |
| L-Leucine | 42.5 |
| L-Lysine•HCl | 82.125 |
| L-Methionine | 13.12 |
| L-Phenylalanine | 22.74 |
| L-Proline | 43.625 |
| L-Serine | 23.625 |
| L-Threonine | 38.726 |
| L-Tryptophan | 6.51 |
| L-Tyrosine•$2Na_2H_2O$ (non-animal) | 35.9 |
| L-Valine | 38.1261 |
| OTHER COMPONENTS | |
| D-Glucose | 3000 |
| HEPES | 1787.25 |
| Na Hypoxanthine | 3.2 |
| Linoleic Acid | 0.066 |
| Lipoic Acid | 0.1525 |
| Phenol Red | 4.675 |
| Na Putrescine•2HCl | 0.191 |
| Na Pyruvate | 137.5 |
| VITAMINS | |
| Biotin | 0.037 |
| Ascorbic Acid | 22.5 |
| D-Ca Pantothenate | 1.37 |
| Choline Chloride | 11.49 |
| Folic Acid | 1.826 |
| i-Inositol | 24.3 |
| Niacinamide | 1.03 |
| Pyridoxine•HCl | 1.046 |
| Riboflavin | 0.13 |
| Thiamine•HCl | 1.23 |
| Thymidine | 0.6325 |
| Vitamin $B_{12}$ | 1.04 |

3. Transfer of Cells to Low Serum Media

Transferring a culture of pancreatic cells to low serum media promotes the selection of a defined population of cells with an intermediate state of differentiation. This cell population will continue to proliferate if subcultured, but maintains high expression levels of pancreatic markers such as PDX-1. Unstimulated, this population secretes relatively low levels of pancreatic endocrine hormones such as insulin, but can be matured according to the methods of the invention to yield high-secreting cells. To transfer a culture of pancreatic cells to low serum medium, the cells may be weaned from high serum to low serum media, or may be placed directly in low serum media following isolation. Medium such as SM95 and SM98 are suitable low serum media, although SM95 yields slightly improved insulin secretion upon maturation the of pancreatic cells.

The CD56 positive cell population and its progeny typically retains both the ability to proliferate and the ability for further differentiation into high-secreting endocrine cells. As the CD56 positive cells proliferate, the strength of CD56 expression can become less pronounced, and in some cases is detectable only by RT-PCR.

The ability of CD56 cells to proliferate provides an advantage in their ability to expand and increase the number of cells available for later maturation into glucose-secreting, insulin-producing aggregates. Proliferative ability is generally assessed by the ability of a culture seeded at a one density to expand to a second density; e.g., cells plated at 180 cells per square centimeter may be expanded to 1,800 cells per ml in a single passage. By repeated cycles of propagation and passage, a starting population of isolated pancreatic cells may be expanded by about 10,000-fold or more (e.g., about 100-fold, 500-fold, 1000-fold, 5000-fold, 10,000-fold, 50,000-fold, 100,000-fold, 500,000-fold, or 1,000,000 fold) while retaining endocrine markers such as PDX-1 and insulin mRNA expression, and retaining the ability to differentiate into mature high-secreting endocrine cells.

IV. Differentiation-Induction of Insulin Producing Aggregates

Cell differentiation of CD56 positive cells can be induced through induction of cell aggregation. As the CD56 positive cells differentiate, the strength of CD56 expression can become less pronounced. Cell aggregation can be induced in a variety of ways. For example, aggregation and differentiation can be induced by growing the cells to confluence. Aggregation and differentiation can also be induced by growing cells on conditioned culture dishes.

A variety of substrates can be used to condition culture dishes. Conditioned culture dishes can be culture dishes that have been used previously to grow intermediate stage pancreatic stem cells. Once the cells have formed a monolayer (typically about 5 days, depending on the initial subculture seeding density), they are removed by trypsinization. Growth of a 100% confluent cell culture is not required to produce a conditioned culture dish. A lowered concentration of trypsin (typically ½ or ¼ of the concentration employed in standard cell culture techniques) is preferred to prevent extensive degradation of the matrix. Alternatively, the cell monolayer may be removed by extracting the substrate with detergent, which will remove the cells but leave behind the secreted matrix (see Gospodarowicz et al., *Proc Natl Acad Sci USA* 77:4094-8 (1980)).

Conveniently, the removed cells which previously grew on the substrate or culture dish may be split and reseeded on the same, now conditioned, culture dish. However, the culture which conditions the substrate and the culture which is seeded on the substrate need not be the same culture. Accordingly, one culture of cells may be grown on a substrate to condition the substrate, the cells removed, and cells from another culture seeded upon the conditioned substrate. The conditioning cells may be from the same or different donor or species as the cells subsequently cultured.

In another embodiment, plates conditioned with collagen coating are used in the invention. Collagen coated plates are commercially available. In a preferred embodiment, collagen IV coated plates are used to induce aggregation and differentiation of pancreatic cells.

Differentiation of CD56 positive cells into mature insulin producing cells can also be enhanced by growth of the cells in the presence of differentiation factors. Preferred differentiation factors include hepatocyte growth factor, keratinocyte growth factor, and exendin-4. Hepatocyte growth factor has been shown to effect differentiation of pancreatic cells in culture and in transgenic animals. See e.g., Mashima, H. et al., *Endocrinology*, 137:3969-3976 (1996); Garcia-Ocana, A. et al., *J. Biol. Chem.* 275:1226-1232 (2000); and Gahr, S. et al., *J. Mol. Endocrinol.* 28:99-110 (2002). Keratinocyte growth factor has been shown to effect differentiation of pancreatic cells in transgenic animals. See e.g., Krakowski, M. L., et al., *Am. J. Path.* 154:683-691 (1999) and Krakowski, M. L., et al., *J. Endochrinol.* 162:167-175 (1999). Exendin-4 has been shown to effect differentiation of pancreatic cells in culture. See e.g., Doyle M. E. and Egan J. M., *Recent Prog. Horm. Res.* 56:377-399 (2001) and Goke, R., et al., *J. Biol. Chem.* 268:19650-19655 (1993). bFGF has been shown to increase the insulin secretion in microencapsulated pancreatic islets. See e.g., Wang W., et al., *Cell Transplant* 10(4-5): 465-471 (2001). IGF-I has an effect on differentiation of pancreatic ductal cells and IGF-I replacement therapy has been used for type I diabetes treatment. See e.g., Smith F E., et al., *Proc. Natl. Acad. Sci. USA.* 15; 88(14): 6152-6156 (1991), Thrailkill K M. et al., *Diabetes Technol. Ther.* 2(1): 69-80 (2000). Evidence has shown that NGF plays an important autoregulatory role in pancreatic beta-cell function. See e.g. Rosenbaum T. et al., *Diabetes* 50(8): 1755-1762 (2001), Vidaltamayo R. et al., *FASEB* 16(8): 891-892 (2002), and Pierucci D. et al., *Diabetologia* 44(10): 1281-1295 (2001). EGF has been shown to promote islet growth and stimulate insulin secretion. See e.g., Chatterjee A K. et al., *Horm. Metab. Res.* 18(12): 873-874 (1986). PDGF has been shown to have an effect on the survival of CD56-positive cells. See e.g., Ben-Hur T. et al., *J. Neurosci.* 18(15):5777-5788 (1998).

V. Characterization of CD56 Positive Cells and their Progeny

Those of skill in the art will recognize that it can be useful to determine the differentiation state of CD56 positive cells and their progeny. The differentiation state of pancreatic cells can be determined in a variety of ways, including measurement of protein and mRNA markers of differentiation and functional assays of pancreatic cells, e.g. ability to secrete insulin in response to glucose stimulation.

A. Phenotypic Assays

To know when mature pancreatic cells are present, it is useful to assay the phenotypes of pancreatic cells at particular stages of culture. Since expression of particular proteins correlates with cell identity or differentiation state, cells may be analyzed for the expression of a marker gene or protein to assess their identity or differentiation state. For example, in freshly isolated pancreatic tissue, expression of amylase identifies the cell as an exocrine acinar cell, while expression of insulin identifies the cell as an endocrine islet cell. Likewise, islet cells at an early stage of differentiation are usually positive for the cytokeratin CK-19, while mature islet cells show less expression of CK-19.

Phenotypic properties may be assayed on a cell-by-cell basis or as a population average. The mode of assay will depend on the particular requirements and methodology of the assay technique. Thus, assays of marker expression by immunohistochemistry, performed on fixed sections or on suspended cells by FACS analysis, measure the frequency and intensity with which individual cells express a given marker. On the other hand, it may be desirable to measure properties such as the average insulin to actin mRNA expression ratio over an entire population of cells. In such cases, the assay is typically performed by collecting mRNA from a pool of cells and measuring the total abundance of insulin and actin messages. Many phenotypic properties may be assayed either on a cell or population basis. For example, insulin expression may be assayed either by staining individual cells for the presence of insulin in secretory granules, or by lysing a pool of cells and assaying for total insulin protein. Similarly, mRNA abundance may be measured over a population of cells by lysing the cells and collecting the mRNA, or on an individual cell basis by in situ hybridization.

1. Cell Differentiation Markers

There are a number of cellular markers that can be used to identify populations of pancreatic cells. Donor cells isolated and cultured begin to display various phenotypic and genotypic indicia of differentiated pancreatic cells. Examples of the phenotypic and genotypic indicia include various molecular markers present in the facultative progenitor cell population that are modulated (e.g., either up or down regulated). These molecular markers include CK-19, which is hypothesized to be a marker of the pancreatic facultative stem cell.

Typically, mammalian stem cells proceed through a number of developmental stages as they mature to their ultimate developmental endpoint. Developmental stages often can be determined by identifying markers present or absent in developing cells. Because human endocrine cells develop in a similar manner, various markers can be used to identify cells as they transition from a stem cell-like phenotype to pseudo-islet phenotype.

The expression of markers in cells induced to proliferate or differentiate by the methods of the present invention bears some similarity to the sequence of marker expression in normal human pancreas development. Very early in development, the primordial epithelial cells express PDX-1, an early cellular marker that is a homeodomain nuclear factor. As the cells develop, they begin to bud out and form a duct. These cells express cytokeratin 19, a marker for epithelial ductal cells, and temporally express PDX-1 leading developmentally to endocrine cells. As these cells continue to develop, they gain the ability to express insulin, somatostatin, or glucagon. The final differentiated cells are only able to express one and become the α cells (glucagon), β cells (insulin), and δ cells (somatostatin). The CD56 positive cell population used herein is believed to be at a less than fully differentiated stage of development, retaining the ability to proliferate and the potential to differentiate into mature endocrine cells. Whether the cells are indeed examples of a precursor in the development pathway or simply a result of in vitro manipulation, the CD56 positive cells are able to proliferate as well as to express endocrine hormones and, therefore, have the potential for being used to correct a deficiency in any type of islet cell.

Markers of interest are molecules that are expressed in temporal- and tissue-specific patterns in the pancreas (see Hollingsworth, *Ann N Y Acad Sci* 880:38-49 (1999)). These molecular markers are divided into three general categories: transcription factors, notch pathway markers, and intermediate filament markers. Examples of transcription factor markers include PDX-1, NeuroD, Nkx-6.1, Isl-1, Pax-6, Pax-4, Ngn-3, and HES-1. Examples of notch pathway markers include Notch1, Notch2, Notch3, Notch4, Jagged1, Jagged2, Dll1, and RBPjk. Examples of intermediate filament markers include CK19 and nestin. Examples of markers of precursors of pancreatic β cells include PDX-1, Pax-4, Ngn-3, and Hb9. Examples of markers of mature pancreatic β cells include insulin, somatostatin, glp-9, and glucagon.

Methods for assessing expression of protein and nucleic acid markers in cultured or isolated cells are standard in the art and include quantitative reverse transcription polymerase chain reaction (RT-PCR), Northern blots, and in situ hybridization (see, e.g., *Current Protocols in Molecular Biology* (Ausubel et al., eds. 2001 supplement)) and immunoassays, such as immunohistochemical analysis of sectioned material, Western blotting, and, for markers that are accessible in intact cells, flow cytometry analysis (FACS) (see, e.g., Harlow and Lane, *Using Antibodies: A Laboratory Manual*, New York: Cold Spring Harbor Laboratory Press (1998)). Conventional histochemical markers of endocrine cell differentiation may also be employed. Cells to be examined by immunohistochemistry may be cultured on glass chamber slides for microscopic examination. Alternatively, cells grown in conventional tissue culture may be manually removed from the culture and embedded in paraffin for sectioning. PDX-1 antibody can be made following the teachings of Leonard J. et al., Mol. Endocrinol., 1993, Oct. 7, (10) 1275-83.

Cell differentiation markers are varied and can be detected by conventional immunohistochemistry. A generally applicable protocol follows.

The staining process begins with removing chamber portion of the slides. Cells were very gently rinsed with in buffers and fixed in paraformaldehyde solution. Cells are then incubated in a blocking solution containing normal serum at room temperature. Cells were permeabilized with non-ionic detergent in blocking solution. Primary antibodies as listed below are prepared in blocking solution at appropriate dilution and added to cells and incubated. Following incubating with primary antibody, cells were rinsed in buffer and reblocked in blocking solution.

Secondary antibody prepared in blocking solution at appropriate dilution is added to the cells and incubated in the dark. Following incubation the cells are rinsed and nuclei were counterstained with Hoechst dye. Excess fluid is removed and the slides are mounted and covered with coverslides. The slides dry and are stored in the dark.

Alternatively the cells can be prepared for immunocytochemistry using the ABC method. In brief, the cells are embedded in paraffin and slides with paraffin sections are dried at 37° C. overnight. The cells are deparaffinized and immersed in a hydrogen peroxide methanol solution to inhibit endogenous peroxidase activity. Slides were boiled in 0.01 citrate buffer (pH 6.0) for 30 minutes to recover certain epitopes. Slides were rinsed with buffer and blocked using normal serum at room temperature in a moist chamber.

Primary antibody prepared in blocking solution are added to the samples and incubated in a moist chamber. Slides are washed and incubated with secondary antibody prepared in blocking solution. Slides were again rinsed with buffer and incubated with Avidin-Horse Reddish Peroxides reagent or ABC complex from a commercial kit (e.g. Dako Corporation). Slides are again rinsed and incubated with diaminobenzidin developing solution; urea hydrogen peroxides in a gold wrap. After washes with distilled water, slides are immersed in Mayer's Hematoxylin for 5 minutes, then kept slides in running tap water until water turned colorless and nuclei were blue. Slides are dehydrated and mounted for viewing.

2. Insulin mRNA Expression

One marker that may be used to characterize pancreatic cell identity, differentiation, or maturity is the level of insulin mRNA. For example, the intermediate cell population of the present invention show expression of insulin mRNA within a defined range. Method for quantitating insulin mRNA include Northern blots, nuclease protection, and primer extension. In one embodiment, RNA is extracted from a population of cultured cells, and the amount of proinsulin message is measured by quantitative reverse transcription PCR. Following reverse transcription, insulin cDNA is specifically and quantitatively amplified from the sample using primers hybridizing to the insulin cDNA sequence, and amplification conditions under which the amount of amplified product is related to the amount of mRNA present in the sample (see, e.g., Zhou et al., *J Biol Chem* 272:25648-51 (1997)). Kinetic quantification procedures are preferred due to the accuracy with which starting mRNA levels can be determined.

Frequently, the amount of insulin mRNA is normalized to a constitutively expressed mRNA such as actin, which is specifically amplified from the same RNA sample using actin-specific primers. Thus, the level of expression of insulin mRNA may be reported as the ratio of insulin mRNA amplification products to actin mRNA amplification products, or simply the insulin:actin mRNA ratio. The expression of mRNAs encoding other pancreatic hormones (e.g., somatostatin or glucagon) may be quantitated by the same method. Insulin and actin mRNA levels can also be determined by in situ hybridization and then used to determine insulin:actin mRNA ratios. In situ hybridization methods are known to those of skill in the art.

B. Functional Assays a. Glucose Stimulated Insulin Secretion

One of the important functions of a beta cell is to adjust its insulin secretion according to the glucose level. Typically, a static glucose stimulation (SGS) assay can be performed on the proliferating adherent pancreatic cells to identify whether they are able to secrete insulin in response to different glucose levels. Cells are generally cultured on an appropriate substrate until nearly confluent. Three days prior to the SGS test, the culture medium is replaced by a medium of similar character but lacking insulin and containing only 1 g/L of glucose. The medium is changed each day for three days and the SGS test is performed on day four.

Before the test, the culture medium may be collected for glucose and insulin analysis. To prepare cells for the test, cells are washed twice with Dulbecco's phosphate-buffered saline (DPBS)+0.5% BSA, incubating for 5 minutes with each wash, and then once with DPBS alone, also incubating for 5 minutes. After washing, the cells are incubated with 10 ml (in a 100 mm dish) or 5 ml (in a 60 mm dish) of Krebs-Ringers SGS solution with 60 mg/dl glucose (KRB-60) for 30 minutes in a 37° C. incubator. This incubation is then repeated.

To perform the SGS assays, cells are incubated in 3 ml (100 mm dish) or 4 ml (T75 flask) or 2 ml (60 mm dish) KRB-60, at 37° C. for 20 minutes. The medium is aspirated and spun, and is collected for insulin assay as LG-1 (low glucose stimulated step). KRB-450+theo (KRB with 450 mg/dl glucose and 10 mM theophylline) is then added with the same volume as above, and cells are cultured under the same condition as above. The supernatant is collected for insulin assay as HG (high glucose stimulated). The cells are then incubated again with KRB-60 and the medium collected as LG-2, and another time as LG-3. The media are collected for insulin analysis, and stored at −20° C. until insulin content is determined by radioimmunoassay (RIA) or other suitable assay.

The results of the SGS test are often expressed as a stimulation index, defined as the HG insulin value divided by the LG-1 insulin value. Generally, a stimulation index of about 2 or greater is considered to be a positive result in the SGS assay, although other values (e.g., 1.5, 2.5, 3.0, 3.5, etc.) may be used to define particular cell populations.

VI. Implantation of CD56 Positive Cells or their Progeny and Restoration of Pancreatic Endocrine Function Those of skill in the art will recognize that propagating CD56 positive cells provide a renewable resource for implantation and restoration of pancreatic function in a mammal. Propagating CD56 positive pancreatic cells are first differentiated before implantation into the mammal. If desired by the user, CD56 cells can be encapsulated before implantation.

A. Encapsulation

Encapsulation of the CD56 positive cells results in the formation of cellular aggregates in the capsules. Encapsulation can allow the pancreatic cells to be transplanted into a diabetic host, while minimizing the immune response of the host animal. The porosity of the encapsulation membrane can be selected to allow secretion of biomaterials, like insulin, from the capsule, while limiting access of the host's immune system to the foreign cells.

Encapsulation methods are known in the art and are disclosed in the following references: van Schelfgaarde & de Vos, *J. Mol. Med.* 77:199-205 (1999), Uludag et al. *Adv. Drug Del Rev.* 42:29-64 (2000) and U.S. Pat. Nos. 5,762,959, 5,550,178, and 5,578,314. Below is a general description of encapsulation of intermediate stage pancreatic stem cells. Specific examples are found in Examples 5 and 9 of this application.

Encapsulation methods are described in detail in co-pending application PCT/US02/41616; herein incorporated by reference.

B. Implantation

Implantation or transplantation into a mammal and subsequent monitoring of endocrine function may be carried out according to methods commonly employed for islet transplantation; see, e.g., Ryan et al., *Diabetes* 50:710-19 (2001); Peck et al., *Ann Med* 33:186-92 (2001); Shapiro et al., *N Engl J Med* 343(4):230-8 (2000); Carlsson et al., *Ups J Med Sci* 105(2):107-23 (2000) and Kuhtreiber, W M, Cell Encapsulation Technology and Therapeutics, Birkhauser, Boston, 1999. Preferred sites of implantation include the peritoneal cavity, the liver, and the kidney capsule.

One of skill in the art will be able to determine an appropriate dosage of microcapsules for an intended recipient. The dosage will depend on the insulin requirements of the recipient. Insulin levels secreted by the microcapsules can be determined immunologically or by amount of biological activity. The recipients body weight can also be taken into account when determining the dosage. If necessary, more than one implantation can be performed as the recipient's response to the encapsulated cells is monitored. Thus, the response to implantation can be used as a guide for the dosage of encapsulated cells. (Ryan et al., *Diabetes* 50:710-19 (2001))

C. In Vivo Measure of Pancreatic Endocrine Function

The function of encapsulated cells in a recipient can be determined by monitoring the response of the recipient to glucose. Implantation of the encapsulated cells can result in control of blood glucose levels. In addition, evidence of increased levels of pancreatic endocrine hormones, insulin, C-peptide, glucagon, and somatostatin can indicate function of the transplanted encapsulated cells.

One of skill in the art will recognize that control of blood glucose can be monitored in different ways. For example, blood glucose can be measured directly, as can body weight and insulin requirements. Oral glucose tolerance tests can also be given. Renal function can also be determined as can other metabolic parameters. (Soon-Shiong, P. et al., *PNAS USA* 90:5843-5847 (1993); Soon-Shiong, P. et al., *Lancet* 343:950-951 (1994)).

All references and patent publications referred to herein are hereby incorporated by reference herein.

As can be appreciated from the disclosure provided above, the present invention has a wide variety of applications. Accordingly, the following examples are offered for illustration purposes and are not intended to be construed as a limitation on the invention in any way.

EXAMPLES

Example 1

Isolation and Initial Culture of Pancreatic Cells
(Passage 1 and 2)

Typically, the CD56 positive pancreatic stem cells are isolated from donor pancreas. A mixed population of isolated pancreatic cells is cultured under conditions to promote the growth of the CD56 positive pancreatic progenitor cells.

Organ Procurement

HD407 adult pancreas was harvested from a 20 year old female organ donor. The organ was digested for islet isolation using the following procedure.

To remove the pancreas from the donor, the abdominal aorta was first cannulated below the junction of renal artery. Portal perfusion was done via cannulation of the inferior mesenteric vein. The cannula was inserted up to and above the junction of the portal vein and the splenic vein. A 2-0 tie was put around the splenic vein at the junction of the portal vein. Another 2-0 tie was put around the splenic artery.

The splenic vein was ligated and cut open on the spleen side immediately before the perfusion was started. This method makes pancreatic perfusion more efficient without building up high pressure, which can damage the islets. It also avoids draining the perfusant from spleen and pancreas into the liver. The lesser sac was opened and normal saline slush was applied to pancreas. After one liter of Aortic perfusion, the splenic artery was ligated.

The pancreas was well-protected when the liver and kidney teams dissected the splenic vein and lower gastric vessels. The pancreas was divided at the edge of duodenum, reducing the risk of damage to the pancreas and also reducing the risk of contamination.

The organ was stored in plastic bag filled with UW solution and set in a Nalgene jar with sterile normal saline slush for transportation.

Isolation of Human Islets from Donor Pancreas

Pancreatic tissue was dissociated by mechanical disruption and digestion with Liberase in HBSS (1.5 mg/ml). Two hundred and forty milliliters of Liberase solution was infused into the pancreas via ductal cannulation. The organ was incubated in an 800 ml tempering beaker, at 37° C. until the tissue became soft, about 10 to 20 minutes.

The main duct was removed from the tissue mass which was then transferred into a metal digestion chamber; automatic circulating digestion was started. When free islets appeared in the sample, 200 ml digestant was collected and 120 ml (0.75 mg/ml) fresh Liberase solution was added into the system for further digestion.

After the majority of islets were released from the surrounding tissue the digestant was collected and diluted with Medium A2 (2% FBS in RPMI). The cells were washed with A10 (10% FBS in RPMI) three times, by centrifugation at 4° C. 1,000 rpm, for two minutes.

Islets were separated from acinar cells by a three-layer density gradient separation in a solution of PIPS (Nycodenz (Nycomed AS, Norway) in UW solution) as described in U.S. Pat. No. 5,739,033.

The pellet of washed pancreatic cells was mixed with 320 ml PIPS (density 1.114) and incubated on ice for 10 minutes. Eight 250 ml flat-bottom centrifuge tubes were filled with 70 ml PIPS (density 1.090). Forty milliliters of cell/PIPS suspension was under-laid into each tube. Sixty milliliters of RPMI with 2% FBS was over-laid on top of the PIPS. Tubes were centrifuged using a Sorvall RC-3C Plus with a 05, ARC rotor at 1,500 rpm, for six minutes without braking.

The upper interface, lower interface (mixture of entrapped islets, fragmental islets, acinar and ductal cells), and the pellet (mainly acinar and ductal cells) were collected separately.

Cells were washed two more times with Medium A10. Cells between density gradients 1,090 and 1,114, which contained about 10% of the islet cells, were collected and seeded in tissue culture flasks. The isolated cells were cultured in a mixture of SM95 and M3 medium at a 4:1 ratio. Within 3-5 days, after cells attached to the flask, the cells were switched to 100% SM95 media. The cells were then sub-cultured on day 8 (passage 1, P1), and sub-cultured again (passage 2, P2) on day 12.

Example 2

Selection of CD56 Positive Cells by FACS Sorting

Isolated pancreatic cells are first incubated with a CD56 specific antibody, followed by incubation with a fluorescently-labeled secondary antibody, specific for the CD56 specific antibody. Labeled CD56 positive cells are separated from CD56 negative cells by FACS.

Four dishes of P2 cells were incubated with 0.5% trypsin/0.2% EDTA (Sigma, T3924) for 5 minutes and washed twice in 4° C. PBS. Cells were then washed through a 40 μM cell strainer. Seven million cells were collected. One million cells were used as an isotype staining control; the rest of the cells were used for FACS sorting.

Cells were blocked with 50% normal goat serum at 4° C. for ten minutes and then stained with a 1:20 dilution of anti-CD56 antibody as primary antibody (Hybridoma Bank of University of Iowa) for one hour at 4° C. The cells were washed with 4° C. PBS twice to remove nonbinding antibody and then blocked with 50% normal goat serum at 4° C. for 10 minutes. The cells were then incubated with 1:100 diluted secondary antibody conjugated with FITC for 30 min.

For the control sample, the above primary antibody was replaced by isotype control antibody, anti-mouse IgG. The other steps were same as above.

The FACS machine, a FACSCalibur system from Becton Dickinson, was sterilized by running 10% bleach for 30 minutes and then sterile PBS for 1 hour before use.

The negative control area of FITC intensity on histogram was determined by running the isotype control sample. To avoid noise signal from cell debris, a gate was created for the main cell population. A histogram was generated from this scan. The stained area was marked as negative area (M1). Any stronger stain intensity beyond the M1 is considered a positive result.

The anti-CD56 antibody stained cells were then FACS scanned to determine the percentage of positive staining in the cell population. The intensity in this scan shifted from M1 to stronger side. The area beyond M1 is considered positive staining and was marked as M2.

A sort gate was created in the M2 area before sorting. Any cells located in the gate were considered CD56-positive and were collected by the machine. CD56-positive cells were collected in tubes coated with 4% BSA and five milliliters of M7 to help maintain cell integrity and viability.

Collected cells were centrifuged at 1200 rpm for five minutes and counted. The collected cells were seeded in two 60 millimeter dishes at a density of approximately $1.4 \times 10^5$ per dish and cultured in Medium #7 initially. Cells were switched to SM95 media for proliferation.

Example 3

Expansion and Differentiation of CD56 Positive Cells

CD56 positive cells can be grown and expanded in culture for up to ten passages. CD56 cells can be induced to differentiate by increasing culture time and by growing cells on culture dishes coated with collagen IV. Differentiation factors, e.g., hepatocyte growth factor, keratinocyte growth factor, exendin-4, basic fibroblast growth factor, insulin-like growth factor-I, nerve growth factor, epidermal growth factor and platelet-derived growth factor;can be added to augment the differentiation process.

Cell Expansion

Passage 3

The FACS-sorted CD56-positive cells were cultured in M7. An estimated 5% of seeded cells attached to the culture dishes after seven days. The cultures were switched to a 25 mixture media of SM95+M7 medias at a 4:1 ratio for three weeks until sub-cultured.

Passage 4

P3 cells were sub-cultured into a single 1×100 mm culture dish (approximately $8.4 \times 10^4$ cells) on day 28 to become passage 4 (P4) cells. The culture of P4 cells was incubated in SM95 media for seven days. During this period the cell growth rate increased significantly.

Passage 5

P4 cells were sub-cultured into two 100 mm culture dishes and a single 60 mm collagen IV coated culture dish. Cells in the 60 mm collagen IV coated culture dish were cultured for one day and fixed for cell identification by in situ insulin mRNA staining.

Passage 6

After six days, the two 100 mm dishes of P5 cells were sub-cultured into two 100 mm culture dishes (P6) and two 6-well plates (P6). One of the 6-well plates was coated with collagen IV. The cells in the 100 mm dishes were cultured in SM95 medium. After seven days, cells from one plate were frozen in liquid nitrogen.

Cells in the 6-well plates were cultured in SM95 for five days and then differentiation or growth factors were added. The following growth factor combinations were used: SM95 only, SM95+50 ng/ml hepatocyte growth factor (HGF or H), SM95+10 ng/ml keratinocyte growth factor (KGF or K), SM95+1 nM Exendin-4 (E), SM95+E+H, and SM95+E+K. Cells were incubated with the growth factors for 48 hours. The plates were fixed and sent for insulin detection by in situ hybridization.

Passage 7

One 100 mm dish of P6 cells was sub-cultured into three 100 mm culture dishes and 2×6-well plates. The original P6 plate was reused for cell culture of P7 cells.

Passage 8

Some of the three 100 mm culture dishes of P7 cells were sub-cultured into three 100 mm dishes to become P8 cells. One of the 100 mm dishes was collagen coated. The remaining P7 cells were sub-cultured into two six-well plates (one collagen IV coated) and two tubes for cryopreservation.

P7 cells from the 6-well collagen IV coated plate were sub-cultured into a second 6-well plate using the same conditions described for passage 6. After incubation, cells were sent for analysis by RT PCR. P7 cells from the uncoated 6-well plate cells were sub-cultured into one 100 mm dish. The 100 mm dish of P8 cells was cultured with SM95.

The P8 cells in the two 6-well plates that were sub-cultured from 100 mm P7 dishes were also grown under the same conditions as P6 cells (one collagen IV coated, one regular). After incubation, the cells were fixed for in situ insulin mRNA staining.

Passage 9

P8 cells from the two uncoated 100 mm culture dishes were sub-cultured into five 100 mm dishes. The cells in the 100 mm collagen IV coated dish were sub-cultured into two 100 mm collagen IV coated dishes.

Part of the cells in the other 100 mm dish was frozen in four tubes and the rests were sub-cultured into two 6-well plates (one collagen IV coated) and cultured in SM95 medium for 5 days, then changed to SM95 media with added factors as listed in passage 6 for two days and fixed for in situ insulin mRNA staining.

Passage 10

Two 100 mm P9 dishes were used for transplantation into two STZ-induced diabetic mice. Two 100 mm P9 dishes were used for CD56 scanning. Two 100 mm P9 dishes were cryopreserved. One 100 mm dish (#9) was subcultured into one 100 mm dish (P10) and cells were also saved for RT-PCR and ICC studies.

Cell Differentiation

Cell differentiation was induced by cell aggregation. Cell aggregation was induced by increasing culture time and coating plates with collagen IV. The differentiation process was augmented by addition of growth and differentiation factors, e.g., hepatocyte growth factor, keratinocyte growth factor, and SM95+1 nM Exendin-4.

Example 4

Characterization of CD56 Sorted Cells and Progeny of CD56 Cells

After two passages, insulin expression was detected in 70% of the CD56 positive cells by in situ hybridization. After five passages (passage 8) an insulin positive clone developed in CD56 positive cells and was detected using in situ hybridization. Both insulin expression and expression of markers of progenitors of β cells were also detected by PCR in CD56 positive cells treated with differentiation factors at passage 8.

In Situ Hybridization

Cell differentiation was determined by insulin expression, as measured by in situ insulin mRNA assay. Some cell aggregates were washed off at the time of media change. The remaining adherent cells were analyzed.

The protocol used was essentially that of Chitnis et al. and Henrique et al. See e.g., Chitnis et al. *Nature* 375:761-766 (1995); and Henrique et al *Nature* 375:787-790 (1995).

Briefly, cultured cells were washed once with PBS and then fixed using 4% formaldehyde in PBS, either for one to two hours at room temp or for two hours to overnight at 4° C. Cells were then washed three times in PBS with 0.1% Tween-20 (PTW). Each wash was ten minutes. Cells were then transferred to 100% MeOH.

Cells were rehydrated with successive washes of 75%, 50%, 25% MeOH/PTW and then washed three times with PTW only. Cells were then treated with 1 μg/ml proteinase K in PTW for 10 minutes at 37° C. using prewarmed solutions. After proteinase K removal, cells were rinsed twice briefly with PTW, and post-fixed for twenty minutes in 4% HCHO+ 0.1% Glutaraldehyde, in PTW. Cells were then rinsed and washed once with PTW.

For pre-hybridization, cells were rinsed once with 1:1 PTW/hybridisation mix and then rinsed with one milliliter hybridisation mix. One milliliter of fresh hybridisation mix was added and cells were incubated with gentle mixing at least one hour at 65° C.

For hybridization, one milliliter pre-warmed hybridization mix with 1 μg/ml DIG-labeled RNA probe was added to the cells. Cells were incubated with gentle mixing at 65° C./overnight.

The following hybridization mix was used.

TABLE 1

| Formamide | 50% | 25 ml |
|---|---|---|
| SSC (20x pH 5 w citric acid!!) | 1.3xSSC | 3.25 ml |
| EDTA (0.5M, pH 8) | 5 mM | 0.5 ml |
| Yeast RNA (20 mg/ml) | 50 μg/ml | 125 μl |
| Tween-20 (10%) | 0.2% | 1 ml |
| CHAPS (10%) | 0.5% | 2.5 ml |
| Heparin (50 mg/ml) | 100 μg/ml | 100 μl |
| $H_2O$ | | 17.5 ml |
| Total | | 50 ml |

After hybridization cells were rinsed twice with hybridization mix pre-warmed to 65° C. Cells were then washed for ten minutes at 65° C. with pre-warmed hybridization mix. Cells were then washed three times for thirty minutes at 65° C. with Washing Solution 1 (50% Formamide/1×SSC/0.1% Tween-20), also prewarmed to 65° C.

A ten minute wash at 65° C. with prewarmed 1:1 Washing solution 1/Maleic Acid Buffer (MABT: 100 mM maleic acid, 150 mM NaCl, 0.1% Tween-20, pH 7.5) followed. Two washes for thirty minutes with MABT followed. Cells were then washed for one hour at room temperature in MABT+2% Boehringer Blocking Reagent.

For secondary antibody, cells were preincubated in two milliliters of MABT+2% BBR+20% heat treated goat serum (65° C. for 30 min), for 1-2 hours. A solution of MABT+2% BBR+20% serum, with a 1/3000 dilution of anti-DIG-AP antibody was added for an overnight incubation at 4° C.

After incubation with secondary antibody, cells were rinsed three times with MABT and then washed three times for one hour with ten to twenty milliliters MABT. Cells were then washed three times for ten minutes with NTMT. (See below.)

Cells were incubated with 1.5 milliliters of NTMT+4.5 μl/ml NBT+3.5 μl/ml BCIP with rocking for first twenty minutes.

Color was developed for a period of thirty minutes to three days. Cells were then washed three times with PTW. Cells were refixed in 4% HCHO/0.1% Glutaraldehyde/PTW, overnight, followed by washes with PTW and storage in PTW/0.1% azide, at +4° C. Cells were then cleared in 50% glycerol/PTW then 80% glycerol/PTW/0.02% azide.

TABLE 2

| NTMT | 5 M NaCl | 1 ml |
|---|---|---|
| | 2M TrisHCl pH 9.5 | 2.5 ml |
| | 2M MgCl$_2$ | 1.25 ml |
| | 10% Tween-20 | 5 ml |
| | H$_2$O | 40.25 ml |
| | Total | 50 ml |

Populations of P2 cells, (e.g., before CD-56 sorting) had very few insulin positive cells. Using in situ hybridization analysis, insulin expression was detected in 70% of CD56-sorted cells at P5. Insulin expression was also detected by in situ hybridization in cells from P6 grown in the absence or presence of various growth factors on collagen IV coated plates or untreated plates.

Insulin positive cells were detected by in situ hybridization in CD56 sorted cells at P8. In addition, an insulin-positive clone was detected in P8 cells grown in the presence of hepatocyte growth factor. Insulin positive cells were still detected by in situ hybridization at P9, although FACS analysis showed CD56 negative cells were present in the P9 cell population.

RT-PCR

PCR was also used to analyze the differentiation state of the cells. Real time RT-PCR was used for analysis of insulin, glucagons, and somatostatin. Regular RT-PCR was used to assay for Hlex9, Pax4, and GLP-1R.

For detection of human Pax4 transcripts, which encode a paired-like homeobox protein, the following PCR primers were used.

```
Forward primer:   5' GAGGCACTGGAGAAAGAGTT 3'
Reverse primer:   5' ACTTGAGCTTCTCTTGCCGA 3'
```

PCR cycles started with a single three minute incubation at 95° C. The following cycle was repeated forty times: thirty seconds at 95° C.; thirty seconds at 55° C.; one minute at 72° C. PCR ended with a five minute extension at 72° C.

For detection of human Hlxb9 transcripts, a homeobox gene, the following PCR primers were used.

```
Forward primer:   5' ATGATCCTGCCTAAGATGCC 3'
Reverse primer:   5' CCATTTCATCCGCCGGTTCTG 3'
```

PCR cycles started with a single three minute incubation at 95° C. The following cycle was repeated forty times: thirty seconds at 95° C.; forty-five seconds at 59° C.; one minute at 72° C. PCR ended with a five minute extension at 72° C.

For detection of human Glp-1R transcripts, which encode a glucagons like peptide receptor, the following PCR primers were used.

```
Forward primer:   5' GTGTGGCGGCCAATTACTAC 3'
Reverse primer:   5' CTTGGCAAGTCTGCATTTGA 3'
```

PCR cycles started with a single three minute incubation at 95° C. The following cycle was repeated forty times: thirty seconds at 95° C.; forty-five seconds at 58° C.; one 25 minute at 72° C. PCR ended with a five minute extension at 72° C.

RT-PCR was used to determine the presence or absence of markers for precursors of beta cells and markers for mature beta cells. Results for markers of mature beta cells, insulin, somatostatin, glucagon, and a glucose transporter isoform (GLUT2) are presented in Table X

TABLE 3

| Samples | insulin | Ins/actin | SST/actin | Glucagon/actin | GLUT2/actin |
|---|---|---|---|---|---|
| YYY⁺P8 SM95, collagen IV | 20800 | 0.027 | 0.0012 | 0.011 | 9.81E−05 |
| YYY⁺P8 SM95 + HGF collagen IV | 17910 | 0.024 | 0.0012 | 0.013 | 8.5E−05 |
| YYY⁺P8 SM95 + KGF, collagen IV | 19020 | 0.036 | 0.0014 | 0.013 | 0.000123 |
| YYY⁺P8 SM95 + exendin-4 collagen IV | 21440 | 0.039 | 0.0026 | 0.024 | 0.000173 |
| YYY⁺P8 SM95 + E + H collagen IV | 16410 | 0.033 | 0.0050 | 0.017 | 8.47E−05 |
| YYY⁺P8 SM95 + E + K collagen IV | 18620 | 0.034 | 0.0013 | 0.018 | 0.00025 |

Progenitor markers for Beta cell and the beta-cell markers were also detected by RT-PCR. Hb-9 and Pax-4 are transcription factors expressed in the precursor beta cells. Both Hb-9 and Pax-4 were detected in all the CD56-sorted cells at P8 on collagen IV plate, treated with various growth factors. Hb-9 was also expressed in mature beta cells.

The GLP-1 receptor is a marker for mature beta cells. GLP-1 receptor transcript was detected in our CD56-sorted cells at P8, which indicates that the CD56 sorted cells have lineage relation to mature β-cells.

Example 5

In Vivo Function of CD56 Positive Cells and their Progeny

Passage 9 cells derived from CD56 positive cells were implanted into SCID mice. After implantation, human C-peptide was detected in the mice indicating the implanted cells secreted insulin in vivo.

Two SCID mice were injected with two million CD56 sorted cells from P9 culture dishes. (E.g., 100 milliliter dish of cells per mouse.) One dish was injected intraperitoneally into SCID mouse #2-22. The other dish was injected subcutaneously into SCID mouse #2-23.

To assess in vivo function of the injected P9 cells, human C-peptide was measured five days after transplantation using an RIA kit from LINCO. Both mice were positive for human C-peptide at day five. The blood Human C-peptide level in SCID mouse #2-22 was 0.1 ng/ml, and in SCID mouse #2-23 was 0.3 ng/ml. This indicates that the CD56 sorted P9 cells had differentiated into mature beta cells and retained their ability to secrete insulin after transplantation.

Example 6

A Time Course Study of the Emergence and Development of CD56+ Cells in Pancreatic Culture HD418 adult pancreas cells were harvested from a 40 year old female donor. The organ was digested as described above. A mixed population of isolated pancreatic cells were either fixed for CD56 staining with a monoclonal antibody against human CD56 (5.1 H11 antibody) before culture or seeded into four well chamber slides for culture in SM95/M7 (1:1). The cultured cells were fixed and stained with 5.1 H11 anti CD56 antibody at day 1, 2, 3, and 9 post seeding.

CD56 expression was determined using immunocytochemical techniques. (Data not shown.) Before culture no CD56 positive cell were detected in the human pancreatic cells enriched with islets. No CD56 positive cells were detected in culture at day one. Detection of CD 56 positive cells begun at 2 days post seeding and CD56 positive cells appeared to increase in cell number from day 2 to day 9.

During the time course, CD56 positive cells largely stayed on top of other cells. CD56 positive cells showed a larger and flattened morphology when they became in direct contact with the plastic surface.

The staining pattern of the CD56 positive cells changed over the time course. At early time points, CD56 staining was evenly distributed throughout the cell surface, but at later time points, the staining became localized to cell borders.

The time course study suggests that, 1) CD56 positive cells emerge as the result of culture, 2) CD56 positive cells are capable of proliferation, and 3) CD56 positive cells undergo dynamic changes in terms of staining patterns and cell morphology in culture.

Example 7

RT-PCR Analysis of CD56 Positively and Negatively Selected Cultured Pancreatic Cells HD421 adult pancreas was harvested from an 11 year old male donor. The organ was digested as described above. HD421 mixed population pancreatic cells at P0 were cultured in SM95/M7 for a week. $10^7$ cells were collected and labeled with 5.1 H1 1 anti-CD56 antibody for FACS sorting. Five hundred thousand CD56 positive cells and five hundred thousand CD56 negative cells were obtained. Cell aliquots of CD56 positive cells, CD56 negative cells, and unsorted cells were collected for RT-PCR analysis. Genes expressed by mature pancreatic endocrine cells (Ins, Gcg, Sst, GLUT-2, Pax6 and Pdxl) and by pancreatic endocrine progenitor cells (Neuro D, Ngn3,) were analyzed. (See e.g., Wilson M. E. et al, Mechanisms of Development 120:65-80 (2003)).

FIG. 1 demonstrates the relative gene expression levels of unsorted cells, CD56 positive cells and CD56 negative cells. Gene expression was expressed as a ratio of mRNA copy number of the gene of interest (such insulin mRNA copy number) over that of β-actin (mRNA copy number of β-actin). For comparison, the levels of gene expression expressed by unsorted cells were normalized to 1, while the levels of gene expressions expressed by CD56 positively sorted and negatively sorted cells were plotted as folds of increase or decrease relative to that of unsorted cells.

FIG. 1 shows that CD56 positive cells have greater endocrine gene expression than do unsorted cells. Additionally, non-sorted cell have higher endocrine gene expression than do CD56 negative cells.

Example 8

Pancreatic Endocrine Phenotype of Cultured Human Pancreatic Cells Derived from CD56 Positive Cells and CD56 Negative Cells The endocrine phenotype of cultured pancreatic cells derived from CD56 positive and CD56 negative cells selected using magnetic beads was analyzed. HD440 adult pancreas was harvested from a 45 year old female donor. The organ was digested as described above. The mixed pancreatic cell population was cultured as described above and similar CD56 expression was seen.

Human pancreatic cells collected from HD440 were cultured first in 8:2 ratio of SM95 and M7. The medium was changed to 100% SM95 at the time of first medium change between 2-3 days post seeding and was used for subsequent cultures. At cell passage 1, cultured cells were separated into CD56 (+) and CD56 (−) populations with EasySep Human Positive Selection Cocktail (StemCell Technology, Vancouver, BC, Canada) by the procedures below:

1. The human pancreatic cells were trypsinized and suspended at a concentration of $1 \times 10^8$ cells/ml in PBS. The cells then were placed in 12×75 mm polystyrene tubes for placement into the EasySep Magnet.
2. EasySep Positive Selection Cocktail (anti CD56 antibody) was added at 100 µl/ml cells, mixed well, and incubated at room temperature for 15 minutes.
3. Magnetic Nanoparticles were added at 50 µl/ml cells, mixed well, and incubated at room temperature for 10 minutes.
4. The cell suspension was adjusted to a total volume of 2.5 ml by adding PBS. The tube was placed into magnet and set aside for 5 minutes.
5. The supernatant fraction containing CD56-negative cells was poured off. The magnetically labeled cells CD56 positive cells remained inside the tube, held by the magnetic field of the EasySep Magnet.
6. The tube was removed from the magnet and 2.5 ml of PBS was added to the cell suspension and mixed well by gently pipetting up and down 2-3 times. The tube was placed back on the magnet and set aside for five minutes.
7. Steps 5 and 6 were repeated twice for a total of three 5-minutes separations in the magnet. The tube was removed from the magnet, suspended the CD56-positive cells were suspended in the cell culture medium SM95, and incubated in a 5% $CO_2$ incubator at 37° C.
8. The supernatants containing CD56-negative cells were combined and centrifuged at 1200 rpm for 3 minutes. Cells were suspended in culture medium SM95, and incubated in a 5% $CO_2$ incubator at 37° C.

Figure 2:
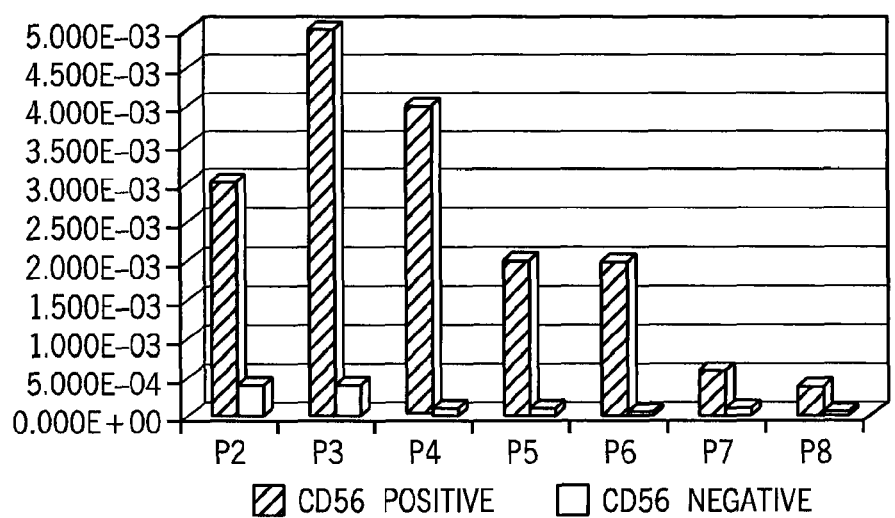
FIG. 2 demonstrates the insulin/β-actin ratios of CD56 positive HD440B cells during proliferation. The CD56 positive cells were selected with magnetic beads.

The CD56 positive and negative cells were cultured separately, until P8, when they were subjected to differentiation treatment. The levels of insulin gene expression of CD56 positive and negative cells from P2 to P8 were analyzed by RT-PCR. The results are shown in FIG. 2. Insulin gene expression was consistently higher in CD56 positive cells than in CD56 negative cells throughout the culture period.

P8 cells were cultured in SM 95 for three days, followed by culture in MM1 differentiation media for three days on coated dishes with Poly-ornithine, and then switched to MM2 for another three days.

Figure 4:
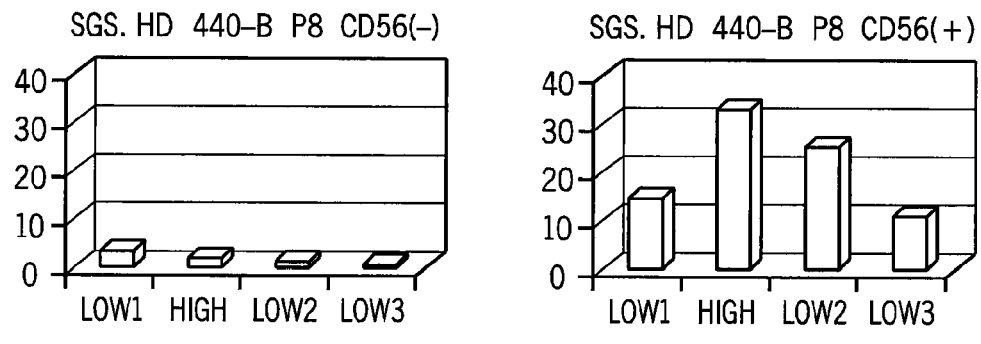
FIG. 4 provides the results of Static Glucose Stimulation (SGS) assays in passage 8 cells derived CD56 negative cells (left panel) and in passage 8 cells derived from CD56 positive cells (right panel).

Step 1:
Media component, MM1: Maturation Medium (FIG. 3)+25 ng/ml bFGF
Dish: 15 µg/ml poly-L-ornithine coated
Cells: After the cells are trypsinized and neutralized, cells are taken from the supernatant.
Cells density: 2 millions/100 mm dish or half millions per well
Time: 3~6 days
Media change; every second day
Step 2:
Media component, MM2: Maturation Medium (FIG. 3)+10 mM Nicotinomide
Dish: 15 µg/ml poly-L-ornithine coated
Time: 3~6 days
Media change: every second day Aggregated cells were assayed for insulin function by using the Static Glucose Stimulation (SGS) assay. CD56 positive cells showed a greater than two fold increase in insulin release in response to glucose challenge. (See, e.g., FIG. 4.) CD56 negative cells did not show an increase in insulin release in response to glucose challenge. (See, e.g., FIG. 4.)

Example 9

Proliferation, Cryopreservation, Differentiation, and Functional Characterization of Cultured Human Pancreatic Cells Derived from CD56 (+) Cells Cultured primary pancreatic cells were FACS sorted at P2 for CD56 positive cells; these cells were continuously cultured as described above. CD56 positive cells at P6 and P8 were cryopreserved and stored in liquid nitrogen. After 15 months of cryopreservation, one vial each of P6 and P8 cells was revived and cultured in a 100 mm tissue culture dishes containing 8 ml of SM95 and 2 ml of M7 media. The two cultures were combined at a subsequent passage to become P8/10. After combination cells were cultured in SM95 media. At P10/12 cells were cultured in SM 95 for three days and passaged into MM1 differentiation media for three days on coated dishes with Poly-ornithine and then switched to MM2 media for another three days. Aggregated cells were collected for RT-PCR in vitro analysis and for transplantation into a diabetic SCID mice for in vivo analysis following alginate encapsulation.

Figure 5:
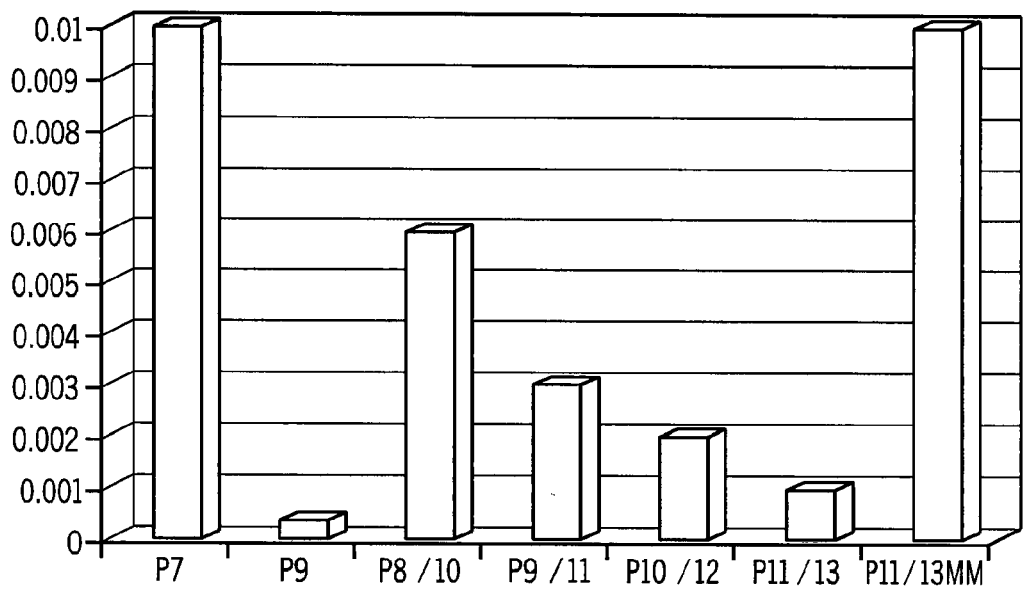
FIG. 5 demonstrates in vitro insulin expression of cells derived from CD56 positive cells that were selected and passaged and then matured at P11/13 in MM media.

Cultured cells collected at P7 and P9 post thawing, but prior to combination, as well as the combined cells collected at P8/10, P9/11, P10/12 and post maturation treatment at P11/13 were analyzed for insulin gene expression by RT-PCR. As shown in FIG. 5, the level of insulin gene expression decreased with passage during the proliferation phase. However, the level of insulin gene expression increased following differentiation treatment at P11/13 suggesting that endocrine precursor cells were present in the culture from CD56 positive cells. Those precursor cells responded to the differentiation treatment to mature into cells that produce higher level of insulin than their predecessors cells.

The high level of insulin gene expression was confirmed by the presence of strong insulin producing cells detected by immuno-cytochemstry (ICC) analysis. (Data not shown.) Strong insulin producing cells were not detected in the proliferating cultures prior to the differentiation treatment.

To test in vivo function, P11/13 post differentiation treated cells were macro-encapsulated and transplanted into STZ induced diabetic mice. Aggregated cells were encapsulated using 2% High G alginate, (batch #V4046-02F). The gel was mixed with cell pellet (1:1) and dropped into MC2 (batch # V4011) solution through an 18 gauge needle and allowed to sit for 5 minutes. The beads were then washed 3 times with MCS (V4008).

Mice were prepared for transplantation with anesthesia consisting of Ketamine 50 mg+Rompun 10 mg/kg BW by intramuscular injection. The animal was skin prepped and a med-line incision was made. The alginate beads were implanted into the peritoneal cavity with a scoop. The wound was closed using 4-0 silk stitches.

Figure 6:
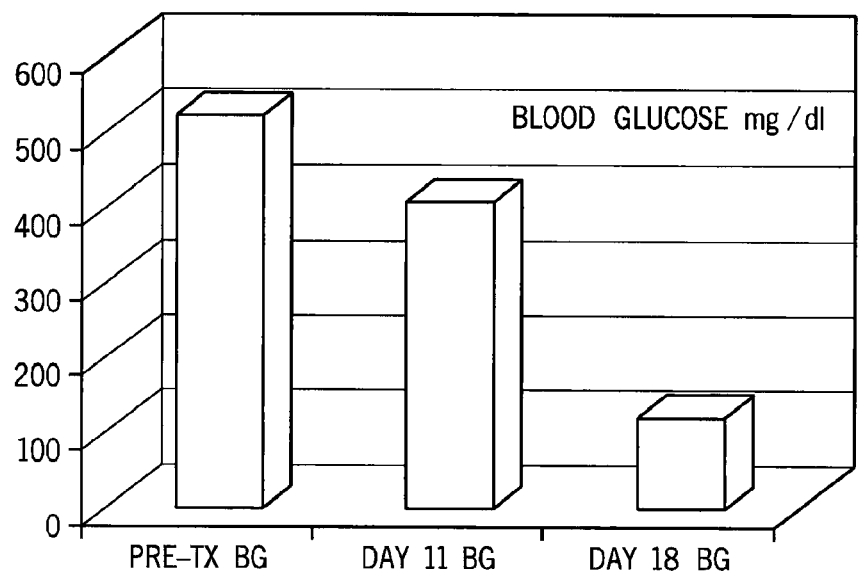
FIG. 6 demonstrates the blood glucose levels of a diabetic SCID mouse that was transplanted with encapsulated, aggregated cells derived from CD56 positive cells.

Cell aggregates derived from cultured HD407 CD56 (+) P11/13 cells were transplanted into the abdominal cavity of diabetic SCID mouse #6 at the dose of approximately 10,000 IEQ/kg. Blood glucose was measured pre- and post-operatively. The result is shown in FIG. 6. Before transplantation, the mouse blood glucose level was 520 mg/dl. On day 11 after transplantation, the mouse blood glucose was reduced to 409 mg/dl. By day 18, mouse blood glucose levels were 121 mg/dl.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A method of obtaining a culture of propagating pancreatic cells that exhibit a CD56 protein as a cell surface marker comprising: (a) isolating a population of cells from a pancreas that include undifferentiated pancreatic cells and differentiated pancreatic cells; (b) contacting the population of cells with a CD56 binding reagent; (c) selecting the undifferentiated pancreatic cells that specifically bind to the CD56 binding reagent, wherein the undifferentiated pancreatic cells can be expanded in culture; and (d) separating the selected, undifferentiated pancreatic cells from the differentiated pancreatic cells that do not bind the CD56 binding reagent to obtain a culture of undifferentiated propagating pancreatic cells that exhibit the CD56 protein as a cell surface marker.

2. The method of claim 1, wherein the CD56 binding reagent is labeled.

3. The method of claim 1, wherein the step of selecting is done by fluorescence activated cell sorting.

4. The method of claim 1, wherein the CD56 binding reagent is an antibody that specifically binds to the CD56 protein.

5. The method of claim 1, wherein the CD56 binding reagent is an antibody that specifically binds to an oligosaccharide linked to the CD56 protein.

6. The method of claim 1, wherein the CD56 binding reagent is a lectin that specifically binds to an oligosaccharide linked to the CD56 protein.

7. The method of claim 1, wherein the CD56 binding reagent is a ligand of the CD56 protein.

8. The method of claim 7, wherein the ligand is selected from the group consisting of soluble CD56, heparin, and heparin sulfate.

9. The method of claim 1, wherein the pancreas is from a human.

10. The method of claim 1, wherein the propagating pancreatic cell culture is differentiated into an aggregate of insulin producing pancreatic cells.

11. The method of claim 10, wherein the step of differentiating the cells comprises culturing the cells on plates coated with collagen IV.

12. The method of claim 10, wherein the step of differentiating the cells comprises culturing the cells in a media comprising a differentiation factor.

13. The method of claim 12, wherein the differentiation factor is selected from the group consisting of hepatocyte growth factor, keratinocyte growth factor, and exendin-4.

14. The method of claim 13, wherein the differentiation factor is hepatocyte growth factor.

* * * * *

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: RT-PCR forward primer for detection of human
      Pax4 paired-like homeobox protein transcripts

<400> SEQUENCE: 1
gaggcactgg agaaagagtt                                             20

<210> SEQ ID NO 2

```
<211> LENGTH: 20
<212> TYPE: DNA
<213> ORGANISM: Artificial Sequence
<220> FEATURE:
<223> OTHER INFORMATION: RT-PCR reverse primer for detection of human
      Pax4 paired-like homeobox proteintranscripts

<400> SEQUENCE: 2
acttgagctt ctcttgccga                                              20

<210> SEQ ID NO 3
<211> LENGTH: 20
<212> TYPE: DNA
<213> ORGANISM: Artificial Sequence
<220> FEATURE:
<223> OTHER INFORMATION: RT-PCR forward primer for detection of human
      progenitor marker transcription factor Hlxb9
      homeobox gene transcripts

<400> SEQUENCE: 3
atgatcctgc ctaagatgcc                                              20

<210> SEQ ID NO 4
<211> LENGTH: 21
<212> TYPE: DNA
<213> ORGANISM: Artificial Sequence
<220> FEATURE:
<223> OTHER INFORMATION: RT-PCR reverse primer for detection of human
      progenitor marker transcription factor Hlxb9
      homeobox gene transcripts

<400> SEQUENCE: 4
ccatttcatc cgccggttct g                                            21

<210> SEQ ID NO 5
<211> LENGTH: 20
<212> TYPE: DNA
<213> ORGANISM: Artificial Sequence
<220> FEATURE:
<223> OTHER INFORMATION: RT-PCR forward primer for detection of human
      Glp-1R glucagon like peptide receptor
      transcripts

<400> SEQUENCE: 5
gtgtggcggc caattactac                                              20

<210> SEQ ID NO 6
<211> LENGTH: 20
<212> TYPE: DNA
<213> ORGANISM: Artificial Sequence
<220> FEATURE:
<223> OTHER INFORMATION: RT-PCR forward primer for detection of human
      Glp-1R glucagon like peptide receptor
      transcripts

<400> SEQUENCE: 6
cttggcaagt ctgcatttga                                              20

<210> SEQ ID NO 7
<211> LENGTH: 34
<212> TYPE: PRT
<213> ORGANISM: Artificial Sequence
<220> FEATURE:
<223> OTHER INFORMATION: Consensus sequence of conserved family of
      hormones
<221> NAME/KEY: VARIANT
<222> LOCATION: 2
<223> OTHER INFORMATION: Xaa = Any Amino Acid
<221> NAME/KEY: VARIANT
```

```
<222> LOCATION: 3
<223> OTHER INFORMATION: Xaa = Ser or Thr
<221> NAME/KEY: VARIANT
<222> LOCATION: (4)...(5)
<223> OTHER INFORMATION: Xaa = Any Amino Acid
<221> NAME/KEY: VARIANT
<222> LOCATION: 6
<223> OTHER INFORMATION: Xaa = Leu, Ile, Val, Met, Phe or Tyr
<221> NAME/KEY: VARIANT
<222> LOCATION: 7
<223> OTHER INFORMATION: Xaa = Any Amino Acid
<221> NAME/KEY: VARIANT
<222> LOCATION: 8
<223> OTHER INFORMATION: Xaa = Leu, Ile, Val, Met, Ser, Thr or Ala
<221> NAME/KEY: VARIANT
<222> LOCATION: (10)...(14)
<223> OTHER INFORMATION: Xaa = Any Amino Acid
<221> NAME/KEY: VARIANT
<222> LOCATION: 15
<223> OTHER INFORMATION: Xaa = Thr, Ala, Leu, Ile or Val
<221> NAME/KEY: VARIANT
<222> LOCATION: (16)...(22)
<223> OTHER INFORMATION: Xaa = Any Amino Acid
<221> NAME/KEY: VARIANT
<222> LOCATION: 23
<223> OTHER INFORMATION: Xaa = Leu, Ile, Val, Met, Phe or Tyr
<221> NAME/KEY: VARIANT
<222> LOCATION: (24)...(29)
<223> OTHER INFORMATION: Xaa = Any Amino Acid
<221> NAME/KEY: VARIANT
<222> LOCATION: 30
<223> OTHER INFORMATION: Xaa = Leu, Ile, Val, Met, Phe or Tyr
<221> NAME/KEY: VARIANT
<222> LOCATION: (31)...(32)
<223> OTHER INFORMATION: Xaa = Any Amino Acid
<221> NAME/KEY: VARIANT
<222> LOCATION: 33
<223> OTHER INFORMATION: Xaa = Any Amino Acid

<400> SEQUENCE: 7

Cys Xaa Xaa Xaa Xaa Xaa Xaa Xaa Pro Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Trp

<210> SEQ ID NO 8
<211> LENGTH: 18
<212> TYPE: PRT
<213> ORGANISM: Artificial Sequence
<220> FEATURE:
<223> OTHER INFORMATION: Consensus sequence of conserved family of
      hormones
<221> NAME/KEY: VARIANT
<222> LOCATION: 2
<223> OTHER INFORMATION: Xaa = Leu, Ile, Val, Met, Phe or Tyr
<221> NAME/KEY: VARIANT
<222> LOCATION: (3)...(4)
<223> OTHER INFORMATION: Xaa = Any Amino Acid
<221> NAME/KEY: VARIANT
<222> LOCATION: 6
<223> OTHER INFORMATION: Xaa = Leu, Ile, Val, Met, Phe, Tyr, Ser, Thr
      or Ala
<221> NAME/KEY: VARIANT
<222> LOCATION: (7)...(11)
<223> OTHER INFORMATION: Xaa = Any Amino Acid
<221> NAME/KEY: VARIANT
<222> LOCATION: 12
<223> OTHER INFORMATION: Xaa = Leu, Ile, Val, Met, Phe or Tyr
<221> NAME/KEY: VARIANT
<222> LOCATION: (13)...(14)
<223> OTHER INFORMATION: Xaa = Any Amino Acid
<221> NAME/KEY: VARIANT
<222> LOCATION: 15
<223> OTHER INFORMATION: Xaa = Leu, Ile, Val, Met, Phe, Tyr or Thr
```

```
<221> NAME/KEY: VARIANT
<222> LOCATION: (16)...(17)
<223> OTHER INFORMATION: Xaa = Any Amino Acid

<400> SEQUENCE: 8

Cys Xaa Xaa Xaa Asp Xaa Xaa Xaa Xaa Xaa Xaa Xaa Xaa Xaa Xaa
1               5                   10                  15

Xaa Cys
```